United States Patent
Schmidt-Ott et al.

(10) Patent No.: US 9,238,837 B2
(45) Date of Patent: Jan. 19, 2016

(54) BIOMARKERS FOR DETERMINATION OF TEMPORAL PHASE OF ACUTE KIDNEY INJURY

(75) Inventors: Kai Schmidt-Ott, Berlin (DE); Anne Wuebken, Berlin (DE)

(73) Assignee: MAX-DELBRUECK-CENTRUM FUER MOLEKULARE MEDIZIN, Berlin (DE)

( * ) Notice: Subject to any disclaimer, the term of this patent is extended or adjusted under 35 U.S.C. 154(b) by 89 days.

(21) Appl. No.: 13/704,652

(22) PCT Filed: Jun. 17, 2011

(86) PCT No.: PCT/EP2011/060125
§ 371 (c)(1),
(2), (4) Date: Mar. 14, 2013

(87) PCT Pub. No.: WO2011/157828
PCT Pub. Date: Dec. 22, 2011

(65) Prior Publication Data
US 2013/0165338 A1    Jun. 27, 2013

Related U.S. Application Data

(60) Provisional application No. 61/355,723, filed on Jun. 17, 2010.

(30) Foreign Application Priority Data

Jun. 17, 2010  (EP) ..................................... 10075261

(51) Int. Cl.
*C12Q 1/68* (2006.01)
*G01N 33/68* (2006.01)

(52) U.S. Cl.
CPC .............. *C12Q 1/6883* (2013.01); *G01N 33/68* (2013.01); *C12Q 2600/112* (2013.01); *C12Q 2600/158* (2013.01)

(58) Field of Classification Search
CPC . G01N 33/68; G01N 33/6893; G01N 33/543; C12Q 1/6883; C40B 30/00; C40B 30/04
USPC ......... 435/6.1, 6.12, 7.1, 7.9; 436/501; 506/7, 506/9
See application file for complete search history.

(56) References Cited

U.S. PATENT DOCUMENTS

2005/0272101 A1* 12/2005 Devarajan et al. ............. 435/7.9

FOREIGN PATENT DOCUMENTS

| WO | 2006/051075 A1 | 5/2006 |
| WO | 2006/094735 A1 | 9/2006 |
| WO | 2009/083950 A2 | 7/2009 |
| WO | 2009/127644 A1 | 10/2009 |

OTHER PUBLICATIONS

Lechler et al., "The Tumor Gene Survivin Is Highly Expressed in Adult Renal Tubular Cells: Implications for a Pathophysiological Role in the Kidney," Am. J. Pathol. 2007, 171:1483-1498.*
Molls Roshni R et al: "Keratinocyte-derived chemokine is an early biomarker of ischemic acute kidney injury", in: American Journal of Physiology: Renal, Fluid and Electrolytephysiology, American Physiological Society, US, vol. 290, No. 5, May 1, 2006, pp. F1187-F1193.
Ronco C: "N-GAL: Diagnosing AKI as soon 1-18 as possible", in: Critical Care, Biomed Central Ltd., London, GB, vol. 11, No. 6, Nov. 6, 2007, pp. 1-2.
Nguyen Mai T et al: "Biomarkers for the 1-18 early detection of acute kidney injury", in: Pediatric Nephrology, Springer Verlag, Berlin, DE, vol. 23, No. 12, Dec. 1, 2008, pp. 2151-2157.
Mishra J et al: "Identification of 1-18 Neutrophil Gelatinase-Associated Lipocalin as a Novel Early Urinary Biomarker for Ischemic Renal Injury", in: Journal of the American Society of Nephrology, Williams and Wilkins, Baltimore, MD, US, vol. 14, Jan. 1, 2003, pp. 2534-2543.
Kindt Nele et al: "Protective role of the inhibitor of apoptosis protein, survivin, in toxin-induced acute renal failure", in: FASEB Journal, Fed. of American Soc. Experimental Biology, US, vol. 22, No. 2, Feb. 1, 2008, pp. 510-521.
Kuchtey John et al: "Angiopoietin-like 7 secretion is induced by glaucoma Stimuli and its concentration is elevated in glaucomatous aqueous humor", in: Investigative Ophthalmology & Visual Science, Association for Research in Vision and Ophthalmology, US, vol. 49, No. 8, Aug. 1, 2008, pp. 3438-3448.
Peek R et al: "Molecular cloning of a new angiopoietinlike factor from the human cornea", in: Investigative Ophthalmology & Visual Science Sep. 1998 LNKD—PUBMED:9727400,, vol. 39, No. 10, Sep. 1, 1998, pp. 1782-1788.

* cited by examiner

*Primary Examiner* — Samuel Woolwine
*Assistant Examiner* — Kaijiang Zhang
(74) *Attorney, Agent, or Firm* — Joyce von Natzmer; Agris & Natzmer LLP

(57) ABSTRACT

The invention relates to a method for determining the temporal phase of acute kidney injury, comprising obtaining a test sample from a subject and measuring the expression level of at least one biomarker selected from the group comprising Chac1, Birc5 and Angptl7. The invention also relates to a method for determining the early early phase, the late early phase, the severity and/or timing of acute kidney injury via analysis of the biomarkers Chac1, Birc5 and/or Angptl7, in addition to a test kit for carrying out said methods and antibodies directed against Chac1, Birc5 or Angptl7.

14 Claims, 6 Drawing Sheets

SEQUENCE LISTING

<160> NUMBER OF SEQ ID NOS: 18

<210> SEQ ID NO 1
<211> LENGTH: 3082
<212> TYPE: DNA
<213> ORGANISM: Homo sapiens

<400> SEQUENCE: 1

| | | | | | | |
|---|---|---|---|---|---|---|
| aaggtttaaa | gggcgcctcc | atgggggggcg | ctcagctgga | gctaccgagc | ggtgccaggc | 60 |
| caggtgtgtg | cgtccgtcgg | tctttccgtg | cccacgccgg | agaccagccc | cggaggccgc | 120 |
| ctgggcctat | ccctgtgcca | ggcaccatga | agcaggagtc | tgcagcccg | aacaccccgc | 180 |
| ccacctcgca | gtcccctacg | ccgtccgctc | agttccccg | aaacgacggc | gaccctcaag | 240 |
| cgctgtggat | tttcgggtac | ggctccctgg | tgtggaggcc | cgacttcgcc | tacagcgaca | 300 |
| gccgtgtggg | cttcgtgcgc | ggctacagcc | gccgtttctg | gcagggagac | accttccatc | 360 |
| ggggcagcga | caagatggtg | agcatccaac | cgtgcccagg | ggagtgaggg | ggttgggggc | 420 |
| gggatactgg | gcgccagtgc | cctggaatgt | ccggggctct | ctgggccaat | agaaagaaat | 480 |
| gtgtaaacct | gtgtctgggg | tttgtggctc | atttaaatgt | atgtgcccag | tgcatcactg | 540 |
| tgatggctgg | agtctgtgaa | cctgtggatc | cctgtgttga | tcaccaactg | ggaccactga | 600 |
| catgtcagtg | tttctggacg | tttctcctac | atccgtgcat | cgctcccca | ccttcccctg | 660 |
| catgaatggg | actcagcatg | cagagtgggg | cacttggagg | cccgggtcag | cgggattgat | 720 |
| aaaggtttcc | ttgctgatgg | cagagctgat | ttctaacttg | tctatttcaa | aatatttctt | 780 |
| ccctccctag | cctggccgtg | tggtgacgct | ccttgaagat | catgaggtaa | gtgcccgaat | 840 |
| catgaagggg | aaccctggcc | cagtgtgaag | gggaccagc | agagagagct | cataggctct | 900 |
| tggctgcagg | ctagctctgt | ctgatgcttc | tctggcagag | tagaaacgtg | ttctagctca | 960 |
| gtgcttctca | ccaaatcaca | tgaggatctt | gttagaatgc | agattttagt | tcagtagcat | 1020 |
| gagaatgggt | cctgagacac | agcattccta | actagcttac | aggtgatgcc | accacatcct | 1080 |
| ggaccacact | tgaggagga | atcctgtctt | ccctggtact | agaccacttt | gtcaactgtt | 1140 |
| ttttttttt | gttgttgttg | ttgttgtttt | gtttgtttgt | ttttgagaca | gagtcttgct | 1200 |
| ctgttgccca | ggctggagtg | cagtgatgca | atcttggctc | actgcaacat | ctgccttcca | 1260 |
| gattcaagcg | attctcccac | ctcagcctcc | cgagtagctg | ggattacagg | catgcgctac | 1320 |
| cacactcagc | taattttgt | attttagta | gagacggagt | tcaccatat | tggccaggct | 1380 |
| ggtctggaac | tcctgatctc | aagtgatctg | cccaccctca | gcctcccaaa | atgctgggat | 1440 |
| tacaggcatg | agctactgca | cctggcctca | actatgcctt | tttttttt | tttaagacgg | 1500 |
| agtcttaccc | ttgtcaccca | ggctgaagtc | actgcaacct | ccacctcctg | ggttcaaacg | 1560 |
| attctactgc | ctcaccctcc | cgagtagctg | ggttacaggc | gtacgccacc | atgcctggct | 1620 |
| aattttgta | tttttagtag | agatgggtt | tcaccatttt | ggccaggccg | gtctcgaaca | 1680 |
| cctgacctga | agtgatccac | ctgccttggc | ctctcaaagt | gttgggatta | caagcatgag | 1740 |
| ccaccacgcc | tggcctttca | actgttctta | acaaagagag | tacaagggct | tgaggtactg | 1800 |
| ccaccagatg | gctcatcagc | cgaccacagc | ctcccttata | gagcacagtc | ctgggtgggg | 1860 |
| gtggcatgtt | aggataggag | agggagcagc | aaggagctgt | catgactgac | cccgggtgtc | 1920 |
| cctatttctt | cccagggctg | cacttggggc | gtggcatacc | aagtgcaagg | ggagcaggta | 1980 |
| agcaaggccc | tgaagtacct | gaatgtgcga | gaggcagtgc | ttggtggcta | cgataccaag | 2040 |
| gaggtcacct | tctatcccca | agatgctcct | gaccaaccac | tgaaggcatt | ggcctatgtg | 2100 |

```
gccacccac agaaccctgg ttacctgggc cctgcgcctg aagaggccat tgccacgcag    2160
atcctggcct gccggggctt ctccggccac aaccttgaat acttgctgcg tctggcagac    2220
ttcatgcagc tctgtgggcc tcaggcgcag gacgagcacc tggcagccat cgtggacgct    2280
gtgggcacca tgttgccctg cttctgcccc accgagcagg ctctggcgct ggtgtgaggg    2340
gctgagcccc tgcggggagt gctcatgtgg acatcagggc agacaccca ctccagtgca    2400 caagacagac ttgcgaccgc ttgagcccac tgagcagata tggtgggtgg ctggaggctt    2460
ctctttctca gtccctgcct gtctgccagc ctgcagctct cctgcttgac actgacttac    2520
tacttgaaac tttatttatt gcaccatgtt ggtgtggtgg gcaggtggag ggcctgccct    2580
ggacacaggg gccctgctga gcagtggccc catcctggaa cttgaccaga ttcccccag    2640 tgctgctgct aacccacac cacccaggcc tccacctccc cagggagtct ccaagagcct    2700
cgatcctctg ctcactcagc ccagccatcc atagccctgg gaattccacc tgccaaggat    2760
cccagcaggc tggatgaggg atagtagggc atgaggagaa ggagccctgt aaggactgag    2820
gccccggcca gcccttctcc tccaccagtt ccccagagca gagctggagc tgatgcctgg    2880
acacagctgc tgagcctggc ctgggcctct tacccacttg gttgttttct tgtccctctg    2940
tctgtctgtc tatctacttg tctgtctggg ccactcctgc ctgtgtgttg gtctattcct    3000
gggaagctca tcactacagg ccctggcaac cttcccagtc tgtcccatac tgttacccat    3060
aaaactatct ctttatctgt gc                                              3082
```

```
<210> SEQ ID NO 2
<211> LENGTH: 264
<212> TYPE: PRT
<213> ORGANISM: Homo sapiens

<400> SEQUENCE: 2

Met Gly Gly Ala Gln Leu Glu Leu Pro Ser Gly Ala Arg Pro Gly Val
1               5                   10                  15

Cys Val Arg Arg Ser Phe Arg Ala His Ala Gly Asp Gln Pro Arg Arg
            20                  25                  30

Pro Pro Gly Pro Ile Pro Val Pro Gly Thr Met Lys Gln Glu Ser Ala
        35                  40                  45

Ala Pro Asn Thr Pro Pro Thr Ser Gln Ser Pro Thr Pro Ser Ala Gln
    50                  55                  60

Phe Pro Arg Asn Asp Gly Asp Pro Gln Ala Leu Trp Ile Phe Gly Tyr
65                  70                  75                  80

Gly Ser Leu Val Trp Arg Pro Asp Phe Ala Tyr Ser Asp Ser Arg Val
                85                  90                  95

Gly Phe Val Arg Gly Tyr Ser Arg Arg Phe Trp Gln Gly Asp Thr Phe
            100                 105                 110

His Arg Gly Ser Asp Lys Met Pro Gly Arg Val Val Thr Leu Leu Glu
        115                 120                 125

Asp His Glu Gly Cys Thr Trp Gly Val Ala Tyr Gln Val Gln Gly Glu
    130                 135                 140

Gln Val Ser Lys Ala Leu Lys Tyr Leu Asn Val Arg Glu Ala Val Leu
145                 150                 155                 160

Gly Gly Tyr Asp Thr Lys Glu Val Thr Phe Tyr Pro Gln Asp Ala Pro
                165                 170                 175

Asp Gln Pro Leu Lys Ala Leu Ala Tyr Val Ala Thr Pro Gln Asn Pro
            180                 185                 190
```

```
Gly Tyr Leu Gly Pro Ala Pro Glu Glu Ala Ile Ala Thr Gln Ile Leu
            195                 200                 205

Ala Cys Arg Gly Phe Ser Gly His Asn Leu Glu Tyr Leu Leu Arg Leu
    210                 215                 220

Ala Asp Phe Met Gln Leu Cys Gly Pro Gln Ala Gln Asp Glu His Leu
225                 230                 235                 240

Ala Ala Ile Val Asp Ala Val Gly Thr Met Leu Pro Cys Phe Cys Pro
                245                 250                 255

Thr Glu Gln Ala Leu Ala Leu Val
            260

<210> SEQ ID NO 3
<211> LENGTH: 3085
<212> TYPE: DNA
<213> ORGANISM: Mus musculus

<400> SEQUENCE: 3
```

| | | | | | |
|---|---|---|---|---|---|
| ggccttcctg | gccggagggt | ttaaagagcg | cctctggagg | gaccactcag | ctggaacgac | 60 |
| cgatcggtgc | caggccaggt | gtacgcgtcc | gtcggtcctt | ccgtgcccgt | gccggagacc | 120 |
| agtctcggag | gccacccggg | tccgtccctg | cgcccggcac | catgaagcag | gagtccgcat | 180 |
| cccagagcac | tccgcctcct | tcactgtccc | ctgcaccatc | atccgcgcag | ccttcctggg | 240 |
| gggatggcga | cccccaagcc | ctgtggattt | tcgggtacgg | ctccctagtg | tggaagccgg | 300 |
| actttgccta | tagtgacagc | cgtgtgggct | tcgttcgtgg | ctatagccga | cggttctggc | 360 |
| agggagacac | cttccatagg | ggcagcgaca | agatggtgag | catccttctg | tgcccagagg | 420 |
| agtggagtgg | ggttggcagg | agagtgggca | ctcgtatcct | ggagtggcag | ggaccctggg | 480 |
| ctaactaaga | gaaaattgta | aacctggttt | gtggtttaaa | tttgtgtgcc | tggaaatcag | 540 |
| gttggtgatt | gcacctgtgg | attcttgtgc | tggttactaa | tctgggccgc | tcgttgtttg | 600 |
| tctcttccac | atctgcccat | cactccatgt | cactcgatga | aggtcctctc | ccaggcttg | 660 |
| gggcttaggc | tggcactctt | tcctcctctt | ccttctcttc | ctcttcttcc | tttccctctt | 720 |
| cctcctcttc | ctcttctctt | cctctccctc | ttcctccttg | ttcttctctt | cctcttcctc | 780 |
| ctcctcctcc | ttttcctcct | cctcttctcc | ccctctttt | tccccctcct | ccatcttacc | 840 |
| tatttcttgc | tatgtggcct | caaacttgtg | acaaatctct | ctctctggtg | ctgaagtgct | 900 |
| ggaactacag | gttcaagtca | aacaggact | aaaggtgtgt | gtgtgtgtgt | gtgtgtgtgt | 960 |
| gtgtgtgtgt | gtgtgtgt | gtgtgttgct | ggagattgaa | tctaaggtct | tgtgcatgac | 1020 |
| aggcaagccc | cccatgtcaa | taaggttcat | tcatagtcct | ttcggaagtg | ctaatatcta | 1080 |
| atttgtcttt | ttcaaaacct | ttcttccctg | tctagcctgg | ccgagtggtg | accctccttg | 1140 |
| aagaccgtga | ggtaagtgtg | cagtcaagaa | gagaatcctg | gggtctgatg | tatcagggtg | 1200 |
| cagagggtca | gagctcttgt | gtggggagag | tggaagtgta | gctagcttac | tccatgcttc | 1260 |
| ttggagaatc | acttgaggga | gggtcttatt | aagatggatt | tctgtgagtt | cagagttatt | 1320 |
| cttggttaca | taatgaatcc | tgggtcagac | accctgtact | atatgagacg | tctcaaaata | 1380 |
| aacaaaactc | aagggaaata | gggtgaaggg | tattgcttct | gggtggctca | gcagccagtc | 1440 |
| aaacacgtta | gtttttttt | aaagcttcat | ggagaaatgg | ctcaggagtc | agaagcacct | 1500 |
| tctgcttctc | caagggcct | ggatttgata | cccagcaccc | acacagtaac | tcacaatctg | 1560 |
| tagctccagt | tccagggaat | cagactcttc | tgactgacca | ccaagatcac | aggtcgccag | 1620 |
| gcacacacgt | ccatacacat | aaaacttcaa | aattacatct | atttgtacat | gcacgcatgt | 1680 |

```
gcacacgctg taggtcagat gtggaagcaa gacgacaaga tggaagtcga ttctttcctc    1740
cgaccattca tgtcccaggg attggactta ggttatctga tcatcaggca tggtagcaac    1800
tacctctatc ccttgagacg tctccccacc ccctccacct cttttataga acataggtgt    1860
ggaatgtgtc tagggaaca ttctagaatg aacacaggac cagcatcaag ctctgtgact    1920
gactggagtg tctctgtttt tccctagggc tgcacttggg gtgtggcata ccaagttcga    1980
ggggagcagg tgaacgaggc cctgaagtac ctgaatgtga gggaagccgt gcttggtggc    2040
tatgacacta aggaagtcac ctttatcct caagacaccc ctgaccaacc cctcacagca    2100
ctggcctatg tggccacccc acagaaccct ggctacctgg ccctgctcc tgaagaggtc    2160
attgccacac agatccttgc ttgccgaggc ttctctggtc acaaccttga gtacttattg    2220
cgtttggcag acttcatgca gctctgtggg cctcaggcac aagatgagca cctgaagcc    2280
attgtggacg ccgtaggaac cctgctaccc tgctcttacc tacctgagca gcctctggca    2340
ctgacctgag gagccaagct cctgcaagaa gtgtctgagt ggtactggtg gacatcagta    2400
tgcagtactt gagatagact tgatggagca agagagagtt gagaaggcat gctgggtggc    2460
caggggcttt gtgtcttatg ccccgcctgt ctgctagcct tcagctcttc cttcattgac    2520
ccttactcac tacttgaacc tttatttatt gcaccatgtt ggtgtggtgg cagggcagg    2580
tgggggacct gccctggatg tgggccctgc agtgcggtgg ctctgcccta gtcctctggt    2640
atgtaaccag aatcccccca ttgctgctgc caattccaca ccaccaggc ctccgtagcc    2700
ccagggaccc tccaagatcg ttgctcctct gtccacccag actacccag ccgtggtagt    2760
atcacctgcc catgttccgg gccttctgga tgagggacag cagagaagga ggcgaagtag    2820
ctcttcaagg gccaagggtc agcatccctc ttcattgacg ggcccggggc agagccggat    2880
cctatgcaca gacacagttc ctgggactgg gcctctcccc catccctctt ttttcatttc    2940
cttatccttt tgtctgtctg cttgtttgtc tggatcactt cctatagacc cattggtctg    3000
ttcctggaaa acactacagt ccttgtccat tctcagttga cccatactgt tacccataaa    3060
ctgtctttca ttacctctgc cagaa                                         3085
```

<210> SEQ ID NO 4
<211> LENGTH: 223
<212> TYPE: PRT
<213> ORGANISM: Mus musculus

<400> SEQUENCE: 4

Met Lys Gln Glu Ser Ala Ser Gln Ser Thr Pro Pro Ser Leu Ser
1               5                   10                  15

Pro Ala Pro Ser Ser Ala Gln Pro Phe Trp Gly Asp Gly Asp Pro Gln
            20                  25                  30

Ala Leu Trp Ile Phe Gly Tyr Gly Ser Leu Val Trp Lys Pro Asp Phe
        35                  40                  45

Ala Tyr Ser Asp Ser Arg Val Gly Phe Val Arg Gly Tyr Ser Arg Arg
    50                  55                  60

Phe Trp Gln Gly Asp Thr Phe His Arg Gly Ser Asp Lys Met Pro Gly
65                  70                  75                  80

Arg Val Val Thr Leu Leu Glu Asp His Glu Gly Cys Thr Trp Gly Val
                85                  90                  95

Ala Tyr Gln Val Arg Gly Glu Gln Val Asn Glu Ala Leu Lys Tyr Leu
            100                 105                 110

Asn Val Arg Glu Ala Val Leu Gly Gly Tyr Asp Thr Lys Glu Val Thr
        115                 120                 125

```
Phe Tyr Pro Gln Asp Thr Pro Asp Gln Pro Leu Thr Ala Leu Ala Tyr
    130                 135                 140

Val Ala Thr Pro Gln Asn Pro Gly Tyr Leu Gly Pro Ala Pro Glu Glu
145                 150                 155                 160

Val Ile Ala Thr Gln Ile Leu Ala Cys Arg Gly Phe Ser Gly His Asn
                165                 170                 175

Leu Glu Tyr Leu Leu Arg Leu Ala Asp Phe Met Gln Leu Cys Gly Pro
            180                 185                 190

Gln Ala Gln Asp Glu His Leu Glu Ala Ile Val Asp Ala Val Gly Thr
        195                 200                 205

Leu Leu Pro Cys Ser Tyr Leu Pro Glu Gln Pro Leu Ala Leu Thr
    210                 215                 220

<210> SEQ ID NO 5
<211> LENGTH: 3571
<212> TYPE: DNA
<213> ORGANISM: Rattus norvegicus
<220> FEATURE:
<221> NAME/KEY: misc_feature
<222> LOCATION: (1374)..(1423)
<223> OTHER INFORMATION: n is a, c, g, or t

<400> SEQUENCE: 5
atgattctgc caggtgcact gccggaccgc ggcggagaca acggtcagac cattgacagg      60
gccttgcggg gagacggcgg gtgcgcgcgc cagttccagg ccggtttcca gtacccgcag     120
cctgacgcaa tcttacgcac ccttgctgca tgccagttct ggggaaacct tctccgccgt     180
tgcatcactc ctgctaggtc tgccatggag gaggagccga ccaatcagc acgcgcgttg      240 gcccaggggc gggctgctct ggtacccact cggagggcgg cgcggttaac cgagaagcaa     300
catccaaagg tgattggcca gaaagagatt tgccccgccc caatcaccgg acagctgga     360 ggcagtcaga gggccttcct ggccggaggg tttaaagagc gcctctggag gaccactca     420 gctggaacga ccgatcggtg ccaggccagg tgtacgcgtc cgtcggtcct tccgtgcccg     480
tgccggagac cagccccgga ggccgcccgg gccgtccct gcgcccggca ccatgaagca     540
ggagtccgca gcccagagca ccccgcctcc ttcactgtcc cctgcaccat ccgcgcagcc     600
ttcctgggag gatggcgacc ccaagcccct gtggattttc gggtacggct ccctagtgtg     660
gaagcctgac tttgcctaca gcgacagccg tgtgggcttc gtacgtggct atagccgacg     720
gttctggcag ggagacacct tccacagggg cagcgataag atggtgagca tccttctgta     780
cccagaggac tggggtgggg ttggcaggag agtgggcacc caagtcctgg aatgtcaggg     840
accctgggtt aactaaggga aatgtgtaaa cctggtttgt ggggtttttt tttttttgt      900 tttgttttg tttttgtttt tttccttttt ttttttttt cccggagct ggggaccgaa       960 cccagggcct tgcgcttcct aggtaagcgc tctaccactg agctaaatcc ccagcccca     1020 ggtttgtggt ttaaatgtgt gtacccagga atcaggttgg tgagtgcacc tgtggattct     1080
tgagctgggc cacccactgt ttgtctcttc catatctgtc catcactcca cgtcactaga     1140
tgaaaggcct tccccaaggc ttgggacatg ggctggcgct cttggctgtt gacagagaca     1200
attactcttc ctcctcttct tcctctccct ctttctcttc ttcctctccc tcttcctctt     1260
ctcttcctcc tcttcttcct ctccctcttc ctctcttcct tctccttttc ccctcctcc     1320 tcgatcttac ctacttcttg ctatgtggcc tcaaacttat gacaaacctc ctcnnnnnn     1380 nnnnnnnnnn nnnnnnnnnn nnnnnnnnnn nnnnnnnnnn nnntcctccc cccccccccc    1440
```

-continued

```
cccgctctct ctgtgtctgt ctctctgtct ctctgtctct gtggtgtgtg tgtgtgtgtg     1500
tgtgtgtgtg tgtgtgtttg ttgctggaga ttgaacctaa aaacttgata ggcaagtgtc     1560
cctgccacta aggtacattc acagtccttt tggaagtgct aatatctaat ttgtcttttt     1620
caaaatcttg ctttcctgtc tagcctggcc gagtggtgac cctccttgaa gatcatgagg     1680
taagtgttca gtcaagaggg gaatcctggg atccaatata tcagggtgca gagggtcaga     1740
gctcttgtgt gggatgagtg aaagtacagc ctagctcact ctgtgcttgg agaatcacct     1800
gagggtcttg ttaagatgga tctctgtgag ttcagagtta ttcttggcta tgtagtgagt     1860
ccagggttag cctgtattat atgagatttt gtctccaaac aaaaatcaag gggaataggg     1920
tgaaaggtat tgcttctggg cagctcaaac aagtcagttt tttaaaaaat gtaatggaga     1980
aatggctcag caaccagaag caccttctgc ttttccaaag ggcctagatt tgatacccag     2040
cacccacaca gtaactcacg atctgtagcc ccaggcccag agaatcagac tcttctggcc     2100
tccaaggtca acaggtctcc aggcacacat aaaatttcaa aattacactt atttgatgtg     2160
cactcatgtg cgcgtgctac aggtcagatg tggaagcaag aggacaaatg tagaagtaaa     2220 ttctttctc ctaccatacc tgccctgtcc ccaggattga acttaggttg tcagttcatc      2280
aggcaaggta gcaactacgt ctacccttg agacagctcc ccacttcccc gacctctatc     2340
atggaacaca ggtgtggagt gtctaggcaa acattctaga atgaaggtgg gaccagcaac     2400
gagcgctgtg actgactgga ggtgtctctg tcttccccca gggctgcact ggggtgtgg     2460 cataccaggt tcgaggggag caggtgagcg aggcactgaa gtacctgaac gtgagagaag     2520
ctgtgcttgg tggctacgac actaaggaag tcaccttta tcctcaagac accctgacc     2580 aacccctcac agcactggcc tatgtggcca ccccacagaa ccctggctac ctgggccctg     2640
ctcccgaaga ggtcattgcc acacagatcc ttgcttgccg aggcttctct ggccacaacc     2700
ttgaatactt gttgcgtttg gcagacttca tgcagctctg tgggcctcag gcacaagatg     2760
agcacctgga agccatcgtg gatgccgtag gaagcttgct gccctgctct tacctctctg     2820
agcagcctct ggcactgatc tgaggagcct tgctcctgca aggagtgtcc ggtggatact     2880
ggtggacatc agcatgcagt acttgagata gacttgatgg acctagagaa agctgagaag     2940
gcatggcggg tggccagggg actttgtgtc ttataccct gcctgcttac tagcctccaa     3000
ctcttccttc attgaccctg acttattact tgaaacttta tttattgcac catgttggtg     3060
tggtgggcag ggcaggtggg ggacctgccc tggatgtggg ccctgctgtg cggtggctct     3120
gccctagtcc tctggtacca accagaatcc ccccacccc attgctgctg ctaatcccac      3180
actacccagg ccccacagc cccagggagc ctccaagagc cttgatcctc tgtccaccca      3240
gagtacccca accctggtaa catcacctgc ccatgttcct ggccttttgg atgagggaga     3300
gcagagaagg aggcgaagta gctcttcaag gaccaaggtc cagcatccct cgtcattgac     3360
cgagtccagg gcagagctgg atcctatgca cagacacagc atcccatgt tttcatttcc      3420 ttatccctct gtctgtctgc ttgtttgtct ggatcacttc ctatagaccc attgatctgt     3480
tcctgggaaa tgtcactaca ggtccttgtc tgttctccgt tgacccacac tgtcatccat     3540
aaactatctt taattacctt tgccggaata t                                    3571
```

<210> SEQ ID NO 6
<211> LENGTH: 222
<212> TYPE: PRT
<213> ORGANISM: Rattus norvegicus

<400> SEQUENCE: 6

```
Met Lys Gln Glu Ser Ala Ala Gln Ser Thr Pro Pro Ser Leu Ser
 1               5                  10                  15

Pro Ala Pro Ser Ala Gln Pro Ser Trp Glu Asp Gly Asp Pro Gln Ala
            20                  25                  30

Leu Trp Ile Phe Gly Tyr Gly Ser Leu Val Trp Lys Pro Asp Phe Ala
                35                  40                  45

Tyr Ser Asp Ser Arg Val Gly Phe Val Arg Gly Tyr Ser Arg Arg Phe
 50                  55                  60

Trp Gln Gly Asp Thr Phe His Arg Gly Ser Asp Lys Met Pro Gly Arg
 65              70                  75                  80

Val Val Thr Leu Leu Glu Asp His Glu Gly Cys Thr Trp Gly Val Ala
                85                  90                  95

Tyr Gln Val Arg Gly Glu Gln Val Ser Glu Ala Leu Lys Tyr Leu Asn
                100                 105                 110

Val Arg Glu Ala Val Leu Gly Gly Tyr Asp Thr Lys Glu Val Thr Phe
            115                 120                 125

Tyr Pro Gln Asp Thr Pro Asp Gln Pro Leu Thr Ala Leu Ala Tyr Val
            130                 135                 140

Ala Thr Pro Gln Asn Pro Gly Tyr Leu Gly Pro Ala Pro Glu Glu Val
145                 150                 155                 160

Ile Ala Thr Gln Ile Leu Ala Cys Arg Gly Phe Ser Gly His Asn Leu
                165                 170                 175

Glu Tyr Leu Leu Arg Leu Ala Asp Phe Met Gln Leu Cys Gly Pro Gln
                180                 185                 190

Ala Gln Asp Glu His Leu Glu Ala Ile Val Asp Ala Val Gly Ser Leu
            195                 200                 205

Leu Pro Cys Ser Tyr Leu Ser Glu Gln Pro Leu Ala Leu Ile
    210                 215                 220

<210> SEQ ID NO 7
<211> LENGTH: 11440
<212> TYPE: DNA
<213> ORGANISM: Homo sapiens

<400> SEQUENCE: 7
cccagaaggc cgcgggggt ggaccgccta agagggcgtg cgctcccgac atgccccgcg    60
gcgcgccatt aaccgccaga tttgaatcgc gggaccgt ggcagaggtg gcggcggcgg    120
catgggtgcc ccgacgttgc cccctgcctg gcagcccttt ctcaaggacc accgcatctc    180
tacattcaag aactggccct tcttggaggg ctgcgcctgc accccggagc gggtgagact    240
gcccggcctc ctggggtccc ccacgcccgc cttgccctgt ccctagcgag gccactgtga    300
ctgggcctcg ggggtacaag ccgccctccc ctccccgtcc tgtccccagc gaggccactg    360
tggctgggcc ccttgggtcc aggccggcct ccctccctg ctttgtcccc atcgaggcct    420
ttgtggctgg gcctcgggt tccggctgc acgtccact cacgagctgt gctgtccctt    480
gcagatggcc gaggctggct tcatccactg ccccactgag aacgagccag acttggccca    540
gtgtttcttc tgcttcaagg agctggaagg ctgggagcca gatgacgacc ccatgtaagt    600
cttctctggc cagcctcgat gggctttgtt ttgaactgag ttgtcaaaag atttgagttg    660
caaagacact tagtatggga gggttgcttt ccaccctcat tgcttcttaa acagctgttg    720
tgaacggata cctctctata tgctggtgcc ttggtgatgc ttacaaccta attaaatctc    780
atttgaccaa aatgccttgg ggtggacgta agatgcctga tgcctttcat gttcaacaga    840
```

```
atacatcagc agaccctgtt gttgtgaact cccaggaacg tccaagtgct tttttttgaga    900
tttttttaaaa aacagtttaa ttgaaatata acctacacag cacaaaaatt acccttttgaa   960
agtgtgcact tcacactttc ggaggctgag gcgggcggat cacctgaggt caggagttca   1020
agacctgcct ggccaacttg gcgaaacccc gtctctacta aaaatacaaa aattagccgg   1080
gcatggtagc gcacgcccgt aatcccagct actcgggagg ctaaggcagg agaatcgctt   1140
gaacctggga ggcggaggtt gcagtgagcc gagattgtgc caatgcactc cagcctcggc   1200
gacagagcga gactccgtca taaaaataaa aaattgaaaa aaaaaaaaga aagaaagcat   1260
atacttcagt gttgttctgg attttttttct tcaagatgcc tagttaatga caatgaaatt   1320
ctgtactcgg atggtatctg tcttttccaca ctgtaatgcc atattctttt ctcaccttt    1380
tttctgtcgg attcagttgc ttccacagct ttaattttttt tcccctggag aatcacccca   1440
gttgtttttc tttttggcca gaagagagta gctgtttttt ttcttagtat gtttgctatg   1500
gtggttatac tgcatccccg taatcactgg gaaaagatca gtggtattct tcttgaaaat   1560
gaataagtgt tatgatattt tcagattaga gttacaactg gctgtctttt tggactttgt   1620
gtggccatgt tttcattgta atgcagttct ggtaacggtg atagtcagtt atacagggag   1680
actcccctag cagaaaatga gagtgtgagc taggggggtcc cttggggaac ccggggcaat   1740
aatgcccttc tctgcccctta atccttacag tgggccgggc acggtggctt acgcctgtaa   1800
taccagcact ttgggaggcc gaggcgggcg gatcacgagg tcaggagatc gagaccatct   1860
tggctaatac ggtgaaaccc cgtctccact aaaaatacaa aaattagcc gggcgtggtg    1920
gtgggcgcct gtagtcccag ctactcggga ggctgaggca ggagaatggc gtgaacccag   1980
gaggcggagc ttgcagtgag ccgagattgc accactgcac tccagcctgg gcgacagaat   2040
gagactccgt ctcaaaaaaa aaaaaaaaag aaaaaaatct ttacagtgga ttacataaca   2100
attccagtga aatgaaatta cttcaaacag ttccttgaga atgttggagg gatttgacat   2160
gtaattcctt tggacatata ccatgtaaca cttttccaac taattgctaa ggaagtccag   2220
ataaaataga tacattagcc acacagatgt ggggggagat gtccacaggg agagagaagg   2280
tgctaagagg tgccatatgg gaatgtggct tgggcaaagc actgatgcca tcaacttcag   2340
acttgacgtc ttactcctga ggcagagcag ggtgtgcctg tggagggcgt ggggaggtgg   2400
cccgtgggga gtggactgcc gctttaatcc cttcagctgc cttccgctg ttgttttgat    2460
ttttctagag aggaacataa aaagcattcg tccggttgcg cttttccttt tgtcaagaag   2520
cagtttgaag aattaaccct tggtgaattt ttgaaactgg acagagaaag agccaagaac   2580
aaaattgtat gtattgggaa taagaactgc tcaaaccctg ttcaatgtct ttagcactaa   2640
actaccttagt ccctcaaagg gactctgtgt tttcctcagg aagcattttt ttttttttc    2700
tgagatagag tttcactctt gttgcccagg ctggagtgca atggtgcaat cttggctcac   2760
tgcaacctct gcctctcggg ttcaagtgat tctcctgcct cagcctccca gtaactggg    2820
attacaggga agtgccacca cacccagcta attttttgtat ttttagtaga gatgggtttt   2880
caccacattg cccaggctgg tcttgaactc ctgacctcgt gattcgccca ccttggcctc   2940
ccaaagtgct gggattacag gcgtgaacca ccacgcctgg cttttttttt tttgttctga   3000
gacacagttt cactctgtta cccaggctgg agtggggtgg cctgatctcg gatcactgca   3060
acctccgcct cctgggctca agtgattgc ctgcttcagc ctcccaagta gccgagatta    3120
caggcatgtg ccaccacacc caggtaattt ttgtattttt ggtagagacg aggtttcacc   3180
atgttggcca ggctggtctt gaactcctga cctcaggtga tccacccgcc tcagcctccc   3240
```

```
aaagtgctga gattataggt gtgagccacc acacctggcc tcaggaagta ttttattttt   3300
taaatttatt tatttatttg agatggagtc ttgctctgtc gcccaggcta gagtgcagcg   3360
acgggatctc ggctcactgc aagctccgcc cccaggttc aagccattct cctgcctcag    3420
cctcccgagt agctgggact acaggcgccc gccaccacac ccggctaatt tttttgtatt   3480
tttagtagag acgggttttc accgtgttag ccaggagggt ctcgatctcc tgacctcgtg   3540
atctgcctgc ctcggcctcc caaagtgctg ggattacagg tgtgagccac cacacccggc   3600 tattttatt tttttgagac agggactcac tctgtcacct gggctgcagt gcagtggtac    3660
accatagctc actgcagcct cgaactcctg agctcaagtg atcctcccac ctcatcctcc   3720
caagtaattg ggactacagg cgcaccccac catgcccacc ttatttattt atttatttat   3780
ttatttattt attttcatag agatgagggt tccctgtgtt gtccaggctg gtcttgaact   3840
cctgagctca agggatcctt ttgcctgggc ctcccaaagt gctgagatta caggcatgag   3900
ccaccgtgcc cagctaggaa tcatttttaa agccctagg atgtctgtgt gattttaaag    3960
ctcctggagt gtggccggta aagtatata ccggtataag taaatcccac attttgtgtc    4020
agtatttact agaaacttag tcatttatct gaagttgaaa tgtaactggg ctttatttat   4080
ttatttattt atttatttat ttttaatttt tttttttgag acgagtctca ctttgtcacc   4140
caggctggag tgcagtggca cgatctcggc tcactgcaac ctctgcctcc cgggtcaag   4200 cgattctcct gccttagcct cccgagtagc tgggactaca ggcacgcacc accatgcctg   4260
gctaattttt gtatttttag tagacggggt ttcaccatgc tggccaagct ggtctcaaac   4320
tcctgacctt gtgatctgcc cgctttagcc tcccagagtg ctgggattac aggcatgagc   4380
caccatgcgt ggtcttttta aaattttttg attttttttt ttttgagac agagccttgc    4440 tctgtcgccc aggctggagt gcagtggcac gatctcagct cactacaagc tccgcctccc   4500
gggttcacgc cattcttctg cctcagcctc ctgagtagct gggactacag gtgcccacca   4560
ccacgcctgg ctaatttttt ttggtatttt tattagagac aaggtttcat catgttggcc   4620
aggctggtct caaactcctg acctcaagtg atctgcctgc ctcggcctcc caaagcgctg   4680
agattacagg tgtgatctac tgcaccaggc ctgggcgtca tatattctta tttgctaagt   4740
ctggcagccc cacacagaat aagtactggg ggattccata tccttgtagc aaagccctgg   4800
gtggagagtc aggagatgtt gtagttctgt ctctgccact tgcagacttt gagtttaagc   4860
cagtcgtgct catgctttcc ttgctaaata gaggttagac ccctatccc atggtttctc    4920 aggttgcttt tcagcttgaa aattgtattc ctttgtagag atcagcgtaa aataattctg   4980
tccttatatg tggctttatt ttaatttgag acagagtgtc actcagtcgc ccaggctgga   5040
gtgtggtggt gcgatcttgg ctcactgcga cctccacctc ccaggttcaa gcgattctcg   5100
tgcctcaggc tcccaagtag ctgagattat aggtgtgtgc caccaggccc agctaacttt   5160
tgtattttta gtagacacag gttttgcca tgttggctaa gctggtctcg aactcctggc    5220
ctcaagtgat ctgcccgcct tggcatccca aagtgctggg attacaggtg tgaaccacca   5280
cacctggcct caatatagtg cttttaagt gctaaggact gagattgtgt tttgtcagga    5340
agaggccagt tgtgggtgaa gcatgctgtg agagagcttc tcacctggtt gaggttgtgg   5400
gagctgcagc gtgggaactg gaaagtgggc tgggatcat cttttccag gtcaggggtc     5460 agccagcttt tctgcagcgt gccatagacc atctcttagc cctcgtgggt cagagtctct   5520
gttgcatatt gtcttttgtt gttttcaca acctttaga aacataaaaa gcattcttag     5580
```

```
cccgtgggct ggacaaaaaa aggccatgac gggctgtatg gatttggccc agcaggccct    5640
tgcttgccaa gccctgtttt agacaaggag cagcttgtgt gcctggaacc atcatgggca    5700
caggggagga gcagagtgga tgtggaggtg tgagctggaa accaggtccc agagcgctga    5760
gaaagacaga gggttttttgc ccttgcaaat agagcaactg aaatctgaca ccatccagtt    5820
ccagaaagcc ctgaagtgct ggtggacgct gcggggtgct ccgctctagg gttacaggga    5880
tgaagatgca gtctggtagg gggagtccac tcacctgttg aagatgtgta ttaagaaaag    5940
tagactttca gggccgggca tggtggctca cgcctgtaat cccagcactt tgggaggccg    6000
aggcgggtgg atcacgaggt caggagatcg agaccatcct ggctaacatg gtgaaacccc    6060
gtctttacta aaaatacaaa aaattagctg ggcgtggtgg cgggcgcctg tagtcccagc    6120
tactcgggag gctgaggcag gagaatggcg tgaacctggg aggtggagct tgcagtgagc    6180
cgagatcgcg ccactgcact ccagcctggg cgacagagcg agactccgtc tcaaaaaaaa    6240
aaaaaaaaag taggctttca tgatgtgtga gctgaaggcg cagtaggcag aagtagaggc    6300
ctcagtccct gcaggagacc tctcggtctc tatctcctga tagtcagacc cagccacact    6360
ggaaagaggg gagacattac agcctgcaag aaaagtaggg agatttaaaa actgcttggc    6420
ttttattttg aactgttttt tttgtttgtt tgttttcccc aattcagaat acagaatact    6480
tttatggatt tgttttttatt actttaatttt tgaaacaata taatcttttt tttgttgttt    6540
ttttgagacg ggtcttact ctgtcaccca ggctgagtgc agtggtgtga tcttggctca    6600
cctcagcctc gaccccctgg gctcaaatga ttctcccacc tcagcttccc aagtagctgg    6660
gaccacaggt gcgtgtgttg cgctatacaa atcctgaaga caaggatgct gttgctggtg    6720
atgctgggga ttcccaagat cccagatttg atggcaggat gcccctgtct gctgccttgc    6780
cagggtgcca ggagggcgct gctgtggaag ctgaggcccg gccatccagg gcgatgcatt    6840
gggcgctgat tcttgttcct gctgctgcct cggtgcttag cttttgaaac aatgaaataa    6900
attagaacca gtgtgaaaat cgatcaggaa ataaatttaa tgtggaaata aactgaacaa    6960
cttagttctt cataagagtt tacttggtaa atacttgtga tgaggacaaa acgaagcact    7020
agaaggagag gcgagttgta gacctgggtg gcaggagtgt tttgtttgtt ttctttggca    7080
gggtcttgct ctgttgctca ggctggagta cagtggcgca atcacagctc actatagcct    7140
cgacctcctg gactcaagca atcctcctgc ctcagcctcc cagtagctgg gactacaggc    7200
gcatgccacc atgcctggct aatttttaaat tttttttttt ctcttttttg agatggaatc    7260
tcactctgtc gcccaggctg gagtgcagtg gcgtgatctc ggctgacggc aagctccgcc    7320
tcccaggttc actccattcg cctgcctcag cctcccaagt agctgggact acaggcgctg    7380
ggattacaaa cccaaaccca aagtgctggg attacaggcg tgagccaccg cacccggcct    7440
gttttgtctt tcaatagcaa gagttgtgtt tgcttcgccc ctacctttag tggaaaaatg    7500
tataaaatgg agatattgac ctccacattg gggtggttaa attatagcat gtatgcaaag    7560
gagcttcgct aatttaaggc ttttttgaaa gagaagaaac tgaataatcc atgtgtgtat    7620
atatatttta aaagccatgg tcatctttcc atatcagtaa agctgaggct ccctgggact    7680
gcagagttgt ccatcacagt ccattataag tgcgctgctg ggccaggtgc agtggcttgt    7740
gcctgaatcc cagcactttg ggaggccaag gcaggaggat tcattgagcc caggagtttt    7800
gaggcgagcc tggcaatgt ggccagacct catctcttca aaaatacac aaaaaattag    7860 ccaggcatgg tggcacgtgc ctgtagtctc agctactcag gaggctgagg tgggaggatc    7920
actttgagcc ttgcaggtca aagctgcagt aagccatgat cttgccactg cattccagcc    7980
```

-continued

```
tggatgacag agcgagaccc tgtctctaaa aaaaaaaaaa ccaaacggtg cactgttttc      8040
ttttttctta tcaatttatt atttttaaat taaattttct tttaataatt tataaattat      8100
aaatttatat taaaaaatga caaattttta ttacttatac atgaggtaaa acttaggata      8160
tataaagtac atattgaaaa gtaatttttt ggctggcaca gtggctcaca cctgtaatcc      8220
cagcactttg ggaggccgtg gcgggcagat cacatgagat catgagttcg agaccaacct      8280
gaccaacatg gagagacccc atctctacta aaaatacaaa attagccggg gtggtggcgc      8340
atgcctgtaa tcccagctac tcgggaggct gaggcaggag aatctcttga acccgggagg      8400
cagaggttgc ggtgagccaa gatcgtgcct ttgcacacca gccaaggcaa caagagcgaa      8460
agtccgtctc aaaaaaaaag taatttttt taagttaacc tctgtcagca aacaaattta      8520
acccaataaa ggtctttgtt ttttaatgta gtagaggagt tagggtttat aaaaaatatg      8580
gtagggaagg gggtccctgg atttgctaat gtgattgtca tttgcccctt aggagagagc      8640
tctgttagca gaatgaaaaa attggaagcc agattcaggg agggactgga agcaaaagaa      8700
tttctgttcg aggaagagcc tgatgtttgc cagggtctgt ttaactggac atgaagagga      8760
aggctctgga cttcctcca ggagtttcag gagaaaggta gggcagtggt taagagcaga      8820
gctctgccta gactagctgg ggtgcctaga ctagctgggg tgcccagact agctggggtg      8880
cctagactag ctgggtactt tgagtggctc cttcagcctg gacctcggtt tcctcacctg      8940
tatagtagag atatgggagc acccagcgca ggatcactgt gaacataaat cagttaatgg      9000
aggaagcagg tagagtggtg ctgggtgcat accaagcact ccgtcagtgt ttcctgttat      9060
tcgatgatta ggaggcagct taaactagag ggagttgagc tgaatcagga tgtttgtccc      9120
aggtagctgg gaatctgcct agcccagtgc ccagtttatt taggtgctct ctcagtgttc      9180
cctgattgtt ttttcctttg tcatcttatc tacaggatgt gactgggaag ctctggtttc      9240
agtgtcatgt gtctattctt tatttccagg caaaggaaac caacaataag aagaaagaat      9300
ttgaggaaac tgcggagaaa gtgcgccgtg ccatcgagca gctggctgcc atggattgag      9360
gcctctggcc ggagctgcct ggtcccagag tggctgcacc acttccaggg tttattccct      9420
ggtgccacca gccttcctgt gggccccta gcaatgtctt aggaaggag atcaacattt       9480 tcaaattaga tgtttcaact gtgctcttgt tttgtcttga aagtggcacc agaggtgctt      9540
ctgcctgtgc agcgggtgct gctggtaaca gtggctgctc ctctctctct ctctcttttt      9600
tgggggctca ttttttgctgt tttgattccc gggcttacca ggtgagaagt gagggaggaa      9660
gaaggcagtg tcccttttgc tagagctgac agctttgttc gcgtgggcag agccttccac      9720
agtgaatgtg tctggacctc atgttgttga ggctgtcaca gtcctgagtg tggacttggc      9780
aggtgcctgt tgaatctgag ctgcaggttc cttatctgtc acacctgtgc ctcctcagag      9840
gacagttttt ttgttgttgt gttttttttgt tttttttttt ttggtagatg catgacttgt      9900
gtgtgatgag agaatggaga cagagtccct ggctcctcta ctgttaaca acatggcttt      9960 cttattttgt ttgaattgtt aattcacaga atagcacaaa ctacaattaa aactaagcac      10020
aaagccattc taagtcattg gggaaacggg gtgaacttca ggtggatgag agacagaat       10080 agagtgatag gaagcgtctg gcagatactc cttttgccac tgctgtgtga ttagacaggc      10140
ccagtgagcc gcggggcaca tgctggccgc tcctccctca gaaaaaggca gtggcctaaa      10200 tccttttttaa atgacttggc tcgatgctgt ggggactgg ctgggctgct gcaggccgtg       10260
tgtctgtcag cccaaccttc acatctgtca cgttctccac acgggggaga gacgcagtcc      10320
```

```
gcccaggtcc ccgctttctt tggaggcagc agctcccgca gggctgaagt ctggcgtaag    10380
atgatggatt tgattcgccc tcctccctgt catagagctg cagggtggat tgttacagct    10440
tcgctggaaa cctctggagg tcatctcggc tgttcctgag aaataaaaag cctgtcattt    10500
caaacactgc tgtggaccct actgggtttt taaaatattg tcagttttc atcgtcgtcc     10560 ctagcctgcc aacagccatc tgcccagaca gccgcagtga ggatgagcgt cctggcagag    10620
acgcagttgt ctctgggcgc ttgccagagc cacgaacccc agacctgttt gtatcatccg    10680
ggctccttcc gggcagaaac aactgaaaat gcacttcaga cccacttatt tctgccacat    10740
ctgagtcggc ctgagataga cttttccctc taaactggga gaatatcaca gtggttttg     10800 ttagcagaaa atgcactcca gcctctgtac tcatctaagc tgcttatttt tgatatttgt    10860
gtcagtctgt aaatggatac ttcactttaa taactgttgc ttagtaattg gctttgtaga    10920
gaagctggaa aaaatggttt ttgtcttcaa ctccttttgca tgccaggcgg tgatgtggat    10980
ctcggcttct gtgagcctgt gctgtgggca gggctgagct ggagccgccc ctctcagccc    11040
gcctgccacg gccttcctt aaaggccatc cttaaaacca gaccctcatg gctaccagca     11100
cctgaaagct tcctcgacat ctgttaataa agccgtaggc ccttgtctaa gtgcaaccgc    11160 ctagacttc tttcagatac atgtccacat gtccatttttt caggttctct aagttggagt    11220
ggagtctggg aagggttgtg aatgaggctt ctgggctatg ggtgaggttc caatggcagg    11280
ttagagcccc tcgggccaac tgccatcctg gaaagtagag acagcagtgc ccgctgccca    11340
gaagagacca gcaagccaaa ctggagcccc cattgcaggc tgtcgccatg tggaaagagt    11400
aactcacaat tgccaataaa gtctcatgtg gttttatcta                          11440
```

<210> SEQ ID NO 8
<211> LENGTH: 142
<212> TYPE: PRT
<213> ORGANISM: Homo sapiens

<400> SEQUENCE: 8

Met Gly Ala Pro Thr Leu Pro Pro Ala Trp Gln Pro Phe Leu Lys Asp
1               5                   10                  15

His Arg Ile Ser Thr Phe Lys Asn Trp Pro Phe Leu Glu Gly Cys Ala
            20                  25                  30

Cys Thr Pro Glu Arg Met Ala Glu Ala Gly Phe Ile His Cys Pro Thr
        35                  40                  45

Glu Asn Glu Pro Asp Leu Ala Gln Cys Phe Phe Cys Phe Lys Glu Leu
    50                  55                  60

Glu Gly Trp Glu Pro Asp Asp Pro Ile Glu His Lys Lys His
65                  70                  75                  80

Ser Ser Gly Cys Ala Phe Leu Ser Val Lys Lys Gln Phe Glu Glu Leu
                85                  90                  95

Thr Leu Gly Glu Phe Leu Lys Leu Asp Arg Glu Arg Ala Lys Asn Lys
            100                 105                 110

Ile Ala Lys Glu Thr Asn Asn Lys Lys Lys Glu Phe Glu Glu Thr Ala
        115                 120                 125

Lys Lys Val Arg Arg Ala Ile Glu Gln Leu Ala Ala Met Asp
    130                 135                 140

<210> SEQ ID NO 9
<211> LENGTH: 6507
<212> TYPE: DNA
<213> ORGANISM: Mus musculus -continued

```
<400> SEQUENCE: 9
gcgggcgagg gcgtggggcc ggggctctcc cggcatgctc tgcggcgcgc ctccgcccgc      60
gcgatttgaa tcctgcgttt gagtcgtctt ggcggaggtt gtggtgacgc catcatggga     120
gctccggcgc tgccccagat ctggcagctg tacctcaaga actaccgcat cgccaccttc     180
aagaactggc ccttcctgga ggactgcgcc tgcaccccag agcgagtgag tcccagcttc     240
cagcgactcc accctgggcc cgacggtgcc ttagttgtgt gacccgggat cagaacccgc     300
tatccccacc ctcgcttcgt actgttagcc aggctgcttt gctctgctct gtcctccacg     360
aggccacccc ccccccccgc tctccccacc tctgcctga accactgtta gcctccgggc     420
ctcttcccac tgtcctcagt tctcggcccg aacgatctc tgggaatcat gggataaggt     480
cagactgttg atcccgctca cgagctgtca ttttcagatg gcggaggctg gcttcatcca     540
ctgccctacc gagaacgagc ctgatttggc ccagtgtttt ttctgcttta aggaattgga     600
aggctgggaa cccgatgaca acccgatgta agtcccacag gctactctcg gtgggtttcc     660
tggtgttccc cttccattga gagccttttg ggttgaactg gagttgggac aaaccatttg     720
tatttagtag aagagcatgc ttcttgctca agtgttccag ttatacagct cagactagtc     780
ttgaattctc aatttctgcc ttggtttcct gagtgttgcc aacatgcatg gttttgcctg     840
aggttttttt gttgtgtttt gtttttgttt taaaacaggg tttgtctgtg cagccttggc     900
tgtcctggaa ctcactctgt agaccaggct ggcctcgaac tcagaaatcc gcctgcctct     960
gcctcccaag tgctgggatt aaaggcgtgc agcaccactg cccaaccaaa ttttaaata    1020 tgttattatt acttaattta tatttctatt tgtgtatgtt tggatgtggg tgtcatggtg    1080
gatgttggtg tcaagacagc ttgggggat aacttctctc ttattgtgtt ggtccctgga    1140
attgagctca ggtgagcagg tttgcagca agcatcctca cctgggccat ttcagtggcc    1200
cctgtttggt ttcagacccc aggagtagga actgaggtgc ttattctaca tatcaaagca    1260
gacctggact ccaggctctc ccagcatccc tcactccctc cctggcatac tttgccccca    1320
actctgaact tccagcccag gaactgggca gcccttcccc ccagaggctc caccctatat    1380
aatccaggca ttttggactt ctcttcttct ctctctacat gtgttctttc tctcaccttc    1440
ccatggtgac tcccctggcc tcagtccttg agcccagtga attcacctgg gagcagcttt    1500
ccaataaacc tgcatttcat aacatctaat ctggcttgaa ttggttcatt taaccagcag    1560
agaaataatt tataatcctg gactatgatt cattaaaaac aggtctattg aaatataatc    1620
catctactgc aaaaatcagt agcttagtga cttttttaagg tcttttttaaa aatctaaaaa    1680 aaaaaaaaaa attaaaaaaa aaaaaaaggc tgagagctgg ctcagaggtt aagaccactt    1740
gttgctttta cagaagaccc aggtttggtt cccagcaccc acctggtggc tcacaatcaa    1800
ttacaactcc agtcccggag gatctgaggc ccccttcttg cttctgagga cactcagcac    1860
acatgggaca catctacaca gagcactcat acatgcaaag caaaatttaa aagaaaaaa    1920 aaaagactta atgttgtctg tctttagagc ttacaagctg tgttctaact gcagtcctgc    1980
attgaatgct gtgacgtacc atatgcagga caagtcctct cacgggcgtg tgtgagttag    2040
cggagttccc tgagtagacg tgtgctaaag ctttatgaac attcctgtaa agtggaatga    2100
tttctagcag gtcttttggag gaattcaaac aatcttgtgt gtgtgtgtgt gtatgcatat    2160
gtacatgtat gtataatata catgcgaagg ttgagggaca atttatagac attggatctg    2220
tctgtctctt ctgtctttct actatgagag tcctaggatg ggactcaagc tgacaagctt    2280
agtgaatttt attttaaaaa aatgtttatg ttgggtatgt cttaggattt cttttgtttg    2340
```

```
tttttatttta ttttattggt ttgttatttg tgggttttttt tgttttgttt ttgagactgg    2400 gttttttgttt gtttgtgtgt gtgtgtgtgt gtgtgtttgt gtgtgttttt gttttcttt     2460 tctatgtagc tctggctatc ctggaactttt gtagaccagg ctaacttgaa ctctgcctcc    2520
tgagtgttgg aattaggggc agtcaccacc actgcctggt cttagggttt ctgttgtaaa    2580
gagacgccat ggccactata aaggaaagca tctaactaac tgaggctggc ttacagtcta    2640
gaggtttagt ccattatcat catggtggtg gagaggtagc taagggttct acagctatat    2700
cagcaggaag agagagtgac actgggcctg gcttaagctt ctgaaacatt aaagcctgtc    2760
tctagtgaca cacttcatcc aacaaggcca cagctcttag tggtgccact ccctattagc    2820
taatggggcc actttcatta aaaccaccac agggtaaggc ggtgtctctg gtggcgcagg    2880
tctttaatcc cagcacttgg gaggcagaaa caggcggatt tctgagttca aggccagcct    2940
ggtctacaga gtgagttcca ggacagccag ggctacacag agaaaccctg tctcgaaaaa    3000
acagaaaaaa aagagaaaag aatgggaag acggggggctg gtgagatggc tcagtgggtg    3060
ggagtgctga ctgctcttcc gaaggtcctg agttcgggtc ccagaggcca catggtggca    3120
cacagccatc tgtgatgagg tctgaccccct cttatggagg gtctgaagac agctacagtg    3180
tacttacata taattaataa atgggtgaat ctttaaaaaa aaagaaaaga aaagaatgg    3240 ggaagacata acagagagaa gatatgctgt gtgggatgtt cctaggacat gtttgagcct    3300
caaatcttgt ccttgacaca gatcagggtg caccaagaga cagccgtgga gatgggagat    3360
agactgtggg tggtgagtag ccctggcact tttgacatgt acgtctattt ttttttttt    3420 tattagagag gagcatagaa agcactcccc tggctgcgcc ttcctcactg tcaagaagca    3480 gatgaagaa ctaaccgtca gtgaattctt gaaactggac agacagagag ccaagaacaa    3540
aattgtatgt atgattgaga ataaggactg agcaaattct gcccccagaa gccctaggga    3600
tctgctcagg aagggtgctt caaaggtggt tcctgagcag gtcaccttcc cacctgagtg    3660
gcaagcattg tcagaagccc ttgtcacagg ctgagccccc agtggtagca ctggtatagg    3720
tagaggcttg gggacatggc agagagtatt ggctgaaggg gacactgagc agacaggtca    3780
gctgagcttt gcctcctgtc acgtgaagtt gattgggaag caggaggcac aggtgagtcc    3840
acagggaggt ggctcccatg cagccaggca tgaagagtca gggtggccag agtccagagc    3900
tcagagtaaa cctgggtcca ttttgactga gaacacccca cattttgcat tggttattca    3960
ctgcaattgt tcgtttatct gaagttcaac tctaagcagg cagcctgggt gctcatctgt    4020
taccctcgaa ctgttttagt gggaggagtc ggggaggggt tcactggcaa acactatacc    4080
tcatcctcga aggatgaccc acagctgacc ctggctcagg tagaggctcc gacctgctgt    4140
cttggttgcc acgtttctc ttcagctgta agttacgttc cttggtggag ggctttgtga    4200
aataactgac tgatgctcaa catagaggat gatggtttgc tgtcaggagg agagggagct    4260
gaagatggtg tttggtcagc gtgctcagac actctgggga tggtcaggtg aggtgggtcc    4320
tgctgctcaa gtccctctta tatagcattc ttttttattt atttatttat tttttgaag    4380 cagagttgag gttcaataaa catatttaat acaagcttag gcacagagtc aaaagaacca    4440
tctatccaga ctcagacccc tctcccaagg tttttttttta aggcatgatt ctctgtgcag    4500
ctctttctgc cctggaattc actctgtagc ccagcctggc ctcaaacctc tgcctcctgg    4560
gtgctgggat taaggcatg ctctcccacc accaggcatc ccttcctgtg tttaaggttg    4620
tagctctggg tctgtggaga tcctaccata aggagcacag ccatatttca gtctttttt    4680
```

-continued

```
ttttcttgtc aatttattaa ttttaaatta agttctctaa tctgtgaaag taactttat    4740
tcttctgtaa taattgtctc acaggcttac tgcccctgtc tgctaaccta ggcctagtcc    4800
tggaagcttc taacctctat acaatctaat ctaggtctag aatgttttca gcctctgaga    4860
ctcactgctg agtaaactca cactttctag ttctttctgg gctctaactg actggttcaa    4920
ctcagctgtt ctgacccaaa ctcttctcca agctgactga ttcaatctgg cttttctctt    4980
cagccttttc tgaattgctc tgtttggctt catactgccg ttggcaatct gttctaatcc    5040
ggctgcttct cattctctgg cttgttctgt cctcacctgt ctctcatttg tgctcttcag    5100
tctgtctgcg cacagctgtg ctagtaagac ggcctcctct cttttctgcg ccctgctcct    5160
tacttcgcct cccctccgct cccttctcag gagagctggg cgtgacctag tctctcaatc    5220
ttcctctgat tcgtcacttt gtctgccact caattagaca tcacttgcaa gcatgggtgc    5280
ttccttctac aaactacctt cattgtttgg gattaaaggt gagtgctaag ggctgagcca    5340
caccacaact agaaacagtt ttttccaat aaacaacaca atcttggggg tcacaatgtg    5400
atcaaatatc ctacaagact aacccgggct tggtgccaca gggtacagtc ctaggatact    5460
agggtacaat cccaaataat ttggctattt ggctggctga aggaggactg aaagttaaaa    5520
gctatcctgg gctacatgaa aaaacatgtt ttttttttgtt ttgttttttt ttttgtttt    5580
tttgttttg gtttttgag atagggtttc tctgtatagc cctggctgtc ctggaactca    5640
ctttgtagac caggctggcc tggaactcag agatccacct gcctctgcct ccgagtgct    5700
gggattaaag gcgtgagcca ccacgcccgg cttgaaaaaa catgtttata tatatatg    5760
tatatatata aaaaatcaag gaaggaaaat tccagtttgt agctcagtaa gtatttgctt    5820
attactattg aggccctagg ttcaattccc agcaatacaa aataataac tttccttta    5880
atgatttatc ttgccacgat ggtgatgaaa ctagcatctc accctggaca ggcaagcctg    5940
gccctctggg ccacaccca gccccttcgt gtctgttcat cattccaggc aaaggagacc    6000
aacaacaagc aaaaagagtt tgaagagact gcaaagacta cccgtcagtc aattgagcag    6060
ctggctgcct aatgctgagc ctttgctgag ataacttgga cctgagtgac atgccacatc    6120
taagccacgc atcccagctt ttccagccag ggcctcctag caggatctta gagaaggaga    6180
cagtggtatt ttgaaactgg atatcaaata ttttggttt tgctttaaag tggctacctc    6240
tctttggttt tgtggctttg ctctattgtg acgtggactt aagcaataag gaagtgatga    6300
agggacagtg ttctctgaca ggacctgtgg gggtcggggt gcctgtgcaa ggtcttggtt    6360
ctgattgtga tatttccata cagggctgct aatgcagccc atgggtaagt gtggttatat    6420
gtgtttgtgc tgataatttt gtcctgatga gttttcctac cacggggtaa cggaataaaa    6480
tcacttgaaa aagtggactg taagctc                                        6507
```

<210> SEQ ID NO 10
<211> LENGTH: 140
<212> TYPE: PRT
<213> ORGANISM: Mus musculus

<400> SEQUENCE: 10

Met Gly Ala Pro Ala Leu Pro Gln Ile Trp Gln Leu Tyr Leu Lys Asn
1               5                   10                  15

Tyr Arg Ile Ala Thr Phe Lys Asn Trp Pro Phe Leu Glu Asp Cys Ala
            20                  25                  30

Cys Thr Pro Glu Arg Met Ala Glu Ala Gly Phe Ile His Cys Pro Thr
        35                  40                  45

```
Glu Asn Glu Pro Asp Leu Ala Gln Cys Phe Phe Cys Phe Lys Glu Leu
 50                  55                  60

Glu Gly Trp Glu Pro Asp Asp Asn Pro Ile Glu His Arg Lys His
 65                  70                  75                  80

Ser Pro Gly Cys Ala Phe Leu Thr Val Lys Lys Gln Met Glu Leu
                     85                  90                  95

Thr Val Ser Glu Phe Leu Lys Leu Asp Arg Gln Arg Ala Lys Asn Lys
            100                 105                 110

Ile Ala Lys Glu Thr Asn Asn Lys Gln Lys Glu Phe Glu Glu Thr Ala
        115                 120                 125

Lys Thr Thr Arg Gln Ser Ile Glu Gln Leu Ala Ala
        130                 135                 140

<210> SEQ ID NO 11
<211> LENGTH: 7901
<212> TYPE: DNA
<213> ORGANISM: Rattus norvegicus

<400> SEQUENCE: 11
atcatgggtg ctccggcgct gcccccgacc tggcagctgt accttaagga ccaccgcatc      60
tccaccttca agaactggcc cttcctggag gattgctcct gcaccccaga gcgggtaagt     120
cggcccctac tcgcacctcg gcgttcatac acagacattt ccgtcccagc ttcaagcgac     180
tccatcctgg gccggacggt gccttagtgg tgggacccgg gatcagaact ccccagcctc     240
gcttcgctct gttagccagt gtactttgct ctgctcagga cggggaaaga ctgctctgtt     300
ctccacgagg ccactccgct ctcccctccc tttacctgaa ccactaaggc tgccctatcc     360
ctactgttag gccccgtaga cctggcctct tcccactgtt cccagaggct gcctcagctc     420
tcggcccgga aagattgctg aaatgctag gataaggtca gactgttgat ccttgctcac      480
gagctgtcct tttcagatgg cggaggctgg cttcatccac tgccctaccg agaatgagcc     540
tgatttggcc cagtgttttt tctgctttaa ggaactggaa ggctgggaac cggatgacaa     600
ccctatgtaa gtcccgccgg ctactctccg agggtttcct ggtgcccccc tcccattggg     660
agtcttttgg gaagaactgg aattgggaca aactatctgt atttggtaga agaacctgct     720
tcttactcat gtgttacaga ctggtcttga acttgttata cagctcacac tggtcttgaa     780
ttctcggttt cctgagtgct gccaacatgc actgttttgc ctgaggtttt gttgttgttg     840
tgttttgttt tgttttttggt tcagataggg ttttctctgt gttgtagctt tggctgtcct    900
ggaactcctt ctgtagacca ggctggcctc aaactcagag atccacctgc ctctgcatcc     960
caagtgctgg cgttaaaggt gtgtgccacc attgcccggc ctgcctgaga ttttttaaaga   1020 tttgctgttg tcgatgttgt taatgtgcac atgtatgtca atttctgccg tgcatgtggg    1080
tatcagatcc ctaggggctg gagttagagt ctgttatgag accccttatg tggggtgctg    1140
ggaactgagg ttctgtggga aagcacctaa ctgaagatct gtggaaaagg gctcctaacc    1200
attgtgccat ctctccagtc ccagatattt ttatattatt attattatta ttattattat    1260
tattattatt attactttat gttttctttt tgtgtgtgtt tggatgaggg tgtcatggtg    1320
gatgtcggag taaagacaac tttgaggagt aagttccctc ctattgtatg tgtccctgga    1380
attgaactcc ggtgaggagg tttggcagca agcatcttta cctgctgggc catttctgtg    1440
gccccagttt gatttcagac ccaggacaa gggactgagg tgcatatttt acataccaaa     1500
aacagacctg gcctccaggt tctcccagca tcccttggtg cctcagggc ataccccacc     1560 cccaccctg aacttttcag cccaggggcc agactgccct tcccccccca agactcctcc    1620
```

-continued

```
ctatataatc cagactttt ggtcttctct ctcctgctct tcctcctctt cccccttctc    1680
tctatgtgcg ctctttctct tcctcttacc ccctctttcc cttctcatgg tgactcccct    1740
ggcctctgtc cttggggcca gtgaattcac ctgagagcag ccttccaatt agcctgcaat    1800
taatatcatc taatctggct tgaattggtt catttcacca gtagagaaat tatttatcag    1860
cccctgacca tgattcttta gaaacagctg tattgaaata gaatccacac actgcagaag    1920
tcactcttcg ggtcttcgct ttgcgtcatt actctgggtt tcattcttat gcttacctgt    1980
ccttctgctt gcccattata cctccagccc tggctctttt ttttttaaga tttatttatt    2040
tatgtataca gcattctgcc tgcatataac acctgcaggc aagaagagga catcagatcc    2100
cattacagat ggctataagc caccatgtgg ttgctgggaa ttgaactcag aacctctgga    2160
agagcagcca aaagacacat taggggttaa aaactcagc accctctgac cagagagaaa    2220
caacaactct ggtgcttttc ttggagagaa aattgaggcc atagaagcat cacttttgtc    2280
agcaaagaag gtgaggggac atgggaggca tgacagacag acacagcaac ctgactgaat    2340
actcaagagc tgtgttttct tttgcctatt taaggctagg tgtcttgctg ggcatggaga    2400
cccacacatg ccacctacct cagcactcag gaggcacttg tggatcagcc tgggctacat    2460
aatgaggccc cgtgtcaaag aaacaaggtc tggggctgga gagatggctc agaggttaag    2520
agcacttgtt gccttgcaga aggcctaggt ttgattagca gcacccacct ggtggctcac    2580
aaccgactac aattccagtg ctgggggatc tgatgcctgc gtctggtttc tgcggacacc    2640
aagcacacac gggagggtga agacttaacg ttgcctgtgt ttggagtttg tgtggctgtg    2700
ttctcactgc agtcctgggc tgagtgttgt gacagagcat agccaggata tggtcccttt    2760
gcaggcgtgt gcgagttagc agagtcctgg attaccgtcc aattgcacct cgttcagaat    2820
ctgtgctaac gttataaaaa cattactgta aactaaaatg atttctagca ggtctttggg    2880
gattcaaaca accttttgtgc gtgtgtgtgt gtgtgtgtgt gtgtgtctgt gtctgtgtgt    2940
gtacacacag gtacatgcat gcacaatata catatgtgat gatgtgcgga ggttgaagga    3000
caatttatag acattagatc tctgtccctc tactctctgg gtcctaggat ggaactcaag    3060
ctgtcaggct tagtgaattt tatttacaaa ttttaggta tgggtgtgtc ttaggatttc    3120
tttttgtttg tttgtttgt tgtttgagac ggttttctg tgcggccctg gctatcctgg    3180
aactctgtaa agcaggctgg gttgaactct gccttctgag tgttgagatt aaaggcggtg    3240
accaccactg cctggatctg ttgtgaagag acactgtggc cacagcatta tgaaggaaag    3300
catttagctg gggctatggt cacagcatta taaaggaaag cattgggtt ggggatttag    3360 ctcagtggta cagtgcttgc ctaggaagca caaggccctg ggttcggtcc ctagctccgg    3420
aaaaaaaaaa aaagaaccaa aaaaaaaaaa aaaaaaaaa agaaaggaaa gcatttagct    3480
ggggctatgg ccacagcatt ataaaggaaa gcatttagct ggggctatgg tcacagcatt    3540
ataaaggaaa gcatttagct ggagctatgg ctgcagcatt ataaaggaaa gcatttaact    3600
ggggctgtct tagcgttcag aggtttagtc cattatcatg gtgcaagcat ggccgtatgc    3660
aggcagactt ggtgctgggg aggcagccga gagtttactt ccatatcagc aggcagcagg    3720
tagagagagt gacactgggc ctggcttgag catctgaaac atcagagcct gtccccagtg    3780
acacacttca tccaacaagg ccacatctct taatagtgcc accccttatt agtctatggg    3840
gccattttca ttaaacccac cacgggggtca ggtggcgtct ctggtggagc attcctttag    3900
tcccaacact gaggggggcag aggcaggtgg atctctgaat tggagaccag cctggtctac    3960
```

```
aaagcaaagt tgtacaaagc ccaggacagc cagggctaca tggagaagct ctgtcttgac      4020
aaacaaaaca aaaatcgtgt agcctcctat tgatcactag agaatccaga aaaatattgt      4080
gaccataagg atggggagac cttacagaga gaagataggc tgtgtgggca ttcctgggac      4140
atgtttgccc ttgatgcagt gcagggtgca ccaaaagaca gccgtggaga tgggagatgg      4200
gctgcaggtt gtgagtggcg gtggcgcttt tgacatggag gtctgttggt ttttctagag      4260
aggagcatag gaagcactcc cctggctgcg ccttccttac agtcaagaag caggtggaag      4320
aactgaccgt cagcgagttt ttgaaactgg acaaacaaag agccaagaac aaaattgtat      4380
gtatgaccga aaataaggac tgagcaagtt cggtccccag aagccctggg gatctgtctc      4440
agggagcacc ctcaacccgg gggagcgtgt gggtaaagac aaacaggact gacctggagt      4500
gtggcttgga gctggcatgc agcagcgagac ctgtcccctc agaatgtgat tcagtggtgg      4560
ttcctgtgta aggtcaccttt cccaactgag tgacaagcat tgtcaggagc ccttatcaca      4620
ggctgatccc cgtggtggca gtggtagagg cttgggaaca tggaatagag aatactgtct      4680
gaaggggaca ctgaagcaga cagggcagca gagctttgcc tcttgtcacg ggccgttaat      4740
tgggaagtag gtggcacagg tgagcccaca gggaggtggc tcccatgcag ccgggcatga      4800
agagtcaagg tggccagagt ccagagctca cagtaaaccc gagtccattg ggacagagag      4860
cagagctcac agtaaacccg agtccactgg gactgagaac accccatgtt ttgcatgggg      4920
ttttcactgc aattgtttgt ctatctgaag tccaaattta tcaggcagtc tgtgttctcc      4980
tctgttaccc tcgcactgtt ttagggggag gatttgggga ggggtttact ggcaaacttc      5040
ctcatgctcg aaggatgacc tccagctgac cctggccggg gcggagacta ggacctgctg      5100
tcctgcttac catggtttca cttcagctgt gagttccgtt cttggtgga gggcattgtg       5160 agataactga ctgataactc agtgtcaagg atgatggttt tctgtcaaca gggaggactg      5220
aagacagtgt tgggtccagc acgctcagac actctgggga tgggcaagtg aggtcggcct      5280
tgctgatcaa agtccccgtt atatagtgtt gttgttgttg tggttgttgt tttgaagcac      5340
agttggagtt caataaacat ttaatactag attgggcaca gagtcaaaag aaccatctct      5400
ccaggctcaa accctctcc caggttttct tttttttttt caaagacagg gtttcatcat       5460
ctagccctgg ctgccctaga actcaggaac tcattatgta gaccaggctg acctcaacat      5520
acagagatcg aaccacttct gcctcctgag tgctgggatt aaaggcatgt gttactatgt      5580
gctttttttt ttaattaatt aatttattca ttttccttaa aaacagaggc tttttaaatt      5640
ttatttattt tttaaagatt tatttatcat atataagtac actgtagctg tcttcagaca      5700
caccagaaga gggcattgga tcccattaca gatgtctgtg agccaccatg tggttgctgg      5760
gaattgaact caggtcctct ggaagagcac tcagtgctct tatctactga gccatctctc      5820
cagcccctgt ttttttttaat ttataatgta ttttatgtgt gggtgttttg tttgtggagg    5880 tcaaagagg gcattgcatt atctagaact ggaaccatca tgtggttgct gggaattgaa       5940
ctcaggtcct ctggagagca gcccgtgctc ttaactgctg tgccctcaca gacccctgag     6000
tgttctttgc tgctgttgtt tgttttctga gtcagggctt ctccttggct gtcctggaac     6060
tcactctgta gtccagctgg cctcaaactc agagattcac ctatctgcct cctgagtgct     6120
gggattaaaa gcatgcccca cgccagtcaa cccttccggt agctctgtgg gtctgtggag     6180
ataccataag gagcacagcc attttttcagt ctttttttttt tcttgtcaac ttatttttaa   6240
attaagttct ctagtctgtg aacgtgactt ttattcttct gtaataattg tcctcttaca     6300
ggctcactgc tcccgtgtgc taacttaggc caagtcctgg aagttttagt ctctgtacaa     6360
```

-continued

```
tctaatctag gcctagcatg gtttcagcct ctgaaacgct tctgaatcaa ctcactcttt      6420
ctagttcttt ctgaactctg gctggatggt tcatctcagc tcttctggct caaatcctct      6480
ccaagctgac tgattcagtc tggcttctct ctcagactcc tgaattgctc tgcttggcct      6540
cgtactacct ttagcaatct gttctcattt tctggctcct tctcattttc tggcttgttc      6600
tgtcttcacc tgcgtctagt ttgttctctt caacgtgtct ctgtaaaaac tctctcagta      6660
aaactgcctc ctctcttccc tctctgcact gcttcttaaa tagcttctcc ttcctccctt      6720
ctcatgggag ttggacatat cgtgttctgt caaatctttc tctgattcgt cactttgtct      6780
gccactcaat tagacatcat ttcacacatg ggtgcttcct tctacaaact aactttacct      6840
tcattgtttg ggattaaagt tgcatgttaa gggcatgtct gtgttccaac cagagtgatt      6900
aaaggtgagt gctaagggct gaactagaaa ccacaactag aaacaggttt ttccagtaaa      6960
caacacaatc ttggggttca atgtgatcga acatcctaca acattaacgc tggcttggtg      7020
ccagggggta cagtcctagg gtgcaatccc atataatttg gtcggctgaa ggaggattga      7080
aagtctaaag ctatgggcta catgaatcct gtgtgagtaa gtgtgtgtgt gtgtgcgtgc      7140
atgcgtgtat caaggaagaa aagttggggc ttgtagctca gtaagtattt gcttgttatg      7200
cttgaggcct aggttcaatt cccagcaata caaaattaat aactttcctt ttagtacttt      7260
gttattttgt tgcgatggtg atgaaactgt ggtgtctccc ttggtaggcg agcccctccc      7320
tctgggccac accgcagccc cattgtgtct gttcgtcatt ccaggcaaag gagaccaaca      7380
acaaacagaa agagttcgag gagaccgcga ggacggtccg ccagtccatt gagcagctgg      7440
ctgccttacg ctgagccttt gctgggcaac ctggacctga gtgacatgcc acggctaagc      7500
cacttgtccc agctttccag gcctgcctgg ccgccttggt gtcttacagg agaccgtgac      7560
atttcgaaac tggacatcag atgatttggg gttttgcttt aaagggggctc agcctgcgtg      7620 gccacctctc tttggttttg tggctttgct ctattgtgac ctggacttaa gcactgagga      7680
agggagtgga tgagggacag gattctctga caggatctat ggggtgggga gggggggtgaa      7740 gggagggttg tgcaaggcct ttctggtctt gatgtttcca tgcctggcag ctgtcgcagc      7800
ccatgtgtag gtgtggttta tatatgtttg tgctgataat tcttctgtcc ttctgatgag      7860
tcctcctacc atggggtaat ggaataaaat aacttaacaa a                          7901
```

<210> SEQ ID NO 12
<211> LENGTH: 142
<212> TYPE: PRT
<213> ORGANISM: Rattus norvegicus

<400> SEQUENCE: 12

```
Met Gly Ala Pro Ala Leu Pro Pro Thr Trp Gln Leu Tyr Leu Lys Asp
1               5                   10                  15

His Arg Ile Ser Thr Phe Lys Asn Trp Pro Phe Leu Glu Asp Cys Ser
            20                  25                  30

Cys Thr Pro Glu Arg Met Ala Glu Ala Gly Phe Ile His Cys Pro Thr
        35                  40                  45

Glu Asn Glu Pro Asp Leu Ala Gln Cys Phe Phe Cys Phe Lys Glu Leu
    50                  55                  60

Glu Gly Trp Glu Pro Asp Asp Asn Pro Ile Glu Glu His Arg Lys His
65                  70                  75                  80

Ser Pro Gly Cys Ala Phe Leu Thr Val Lys Lys Gln Val Glu Glu Leu
                85                  90                  95
```

```
              Thr Val Ser Glu Phe Leu Lys Leu Asp Lys Gln Arg Ala Lys Asn Lys
                          100                 105                 110

Ile Ala Lys Glu Thr Asn Asn Lys Gln Lys Glu Phe Glu Glu Thr Ala
                      115                 120                 125

Arg Thr Val Arg Gln Ser Ile Glu Gln Leu Ala Ala Leu Arg
                  130                 135                 140

<210> SEQ ID NO 13
<211> LENGTH: 6641
<212> TYPE: DNA
<213> ORGANISM: Homo sapiens

<400> SEQUENCE: 13
cttgtggagc attcgggctt ggaaggaaag ctataggcta cccattcagc tccctgtca      60 gagactcaag ctttgagaaa ggctagcaaa gagcaaggaa agagagaaaa caacaaagtg     120
gcgaggccct cagagtgaaa gcgtaaggtt cagtcagcct gctgcagctt tgcagacctc     180
agctgggcat ctccagactc ccctgaagga agagccttcc tcacccaaac ccacaaaaga     240
tgctgaaaaa gcctctctca gctgtgacct ggctctgcat tttcatcgtg gcctttgtca     300
gccacccagc gtggctgcag aagctctcta agcacaagac accagcacag ccacagctca     360
aagcggccaa ctgctgtgag gaggtgaagg agctcaaggc ccaagttgcc aaccttagca     420
gcctgctgag tgaactgaac aagaagcagg agagggactg ggtcagcgtg gtcatgcagg     480
tgatggagct ggagagcaac agcaagcgca tggagtcgcg gctcacagat gctgagagca     540
agtactccga gatgaacaac caaattgaca tcatgcagct gcaggcagca cagacggtca     600
ctcagacctc cgcaggtaag gagaccagtc cctgaggga gcgtggagtg cctccccatc      660
tacagcactg cttctacata tcctggtcat cagaaccact actggggcct cttttgtggg     720
tacactttcc ctttagtaaa ggcttatgca gtatttcctt tgacttctaa tgctatgtaa     780
gtttacctaa caccttcacg ggtctctttt atccacacag tgtttcagcc taccatcttg     840
gagtgctgag atactacatg gtttgcccaa agtcacccag caagtcttag aagcagggtt     900
caagtcttcc tgattggtgt agctctgcta cttcctcacc aagagctgac aggctatatc     960
tcaagaaatt ccaaggaagc accaaactgt aacagctgtt cctctggaag caaagttttg    1020
ccagaaacag ttctctggtg ttcctaagat ttaccaggaa tgagcattaa tggaattttg    1080
tgtcctctct ctgtaaacgt aactcttctc attggctcag agttaagtgt agagacacat    1140
aaccatgtga agagtccctt tgtgttcagg aaggatgcgg ctccttaagg ttcctcaatt    1200
gtgatacgtc tatttttttc catggtctta aatgaatttc tccgaataca ggattttta    1260 aatgcaatgc tgaaatatag acttaatagg ccaaaaataa gataaattta atctttcttt    1320
tgcaaaataa ctttatttc tggttagctc agctcaggtg ggccaacatg aatttacggt    1380
ttagagataa aaatttggtt ttctgaaatt atcaggaaaa tattagttgt aaggagcata    1440
tcctatagac atgtcatttc ttgctgatat aaaaaccatt ggtccccatta taaactacat    1500 gaagaacaaa gacatgatca gcttctactg actaagtcaa tggttaacct cagctcaaat    1560
taagaaaaag ttttaacatg aaaccaagct tgaaaattct gttacctgaa ccaacatgta    1620
tcaatcactt tctaagcatg gacttccggg ccctcagttt gggattagaa aggtattctc    1680
aggccatttt ccagacaagt gagtcctgat ttggtctgtg agatgaaacc agacatgcgg    1740
aagaccaggc cagacagagg aatctgaccg tgccacttcc tgctcatcca aacaggaggc    1800
tttctcacca tcctgcaagg aggttcttgg ggtcaagtgc agctctccca ccaggtctct    1860
```

```
tgctcttctt gcccaggaca tcattcctta tttttcttct ctatgaccaa gtgctcagtt    1920
acccttatat tctataagta ggtagtccct tagaggaagc agtaagttgg tgctttcacc    1980
actaagacga aatgaagaat agtgatggcg aaggcacacg tactctacct cccttteccca   2040 aggtgctctg caagagaacc tatgtgcctc agacaactcc catctgccat cttggtgctc    2100
ctctctaagg tcccagtgca gtggtcacca agaaaagcac cccgagacat agcaggcagg    2160
aagcttctct tggatagtaa gggccgcagt ctctgaatcc tatcagaaaa ggctgtctct    2220
tccactatgc tctttgatat ttagaataca gagcttaaat cctgcataaa gtagcagctc    2280
catggcccta gagtaaaaaa actggccagt ctgatgctct catttcattg ttttaacaaa    2340
acttctggga ggaaggcctc aaaggttctt ctgagtgttt tgaggtgcta gctggatgga    2400
aggggaaaat atgtgataat aaaatctatc tcccttaatt atggtctcag gtggcagtag    2460
ccaccatctc tgaacaacaa caaaaacaac caaccaggaa acatcaacaa aaccagactc    2520
tatgagatat tcacgactga tttgttatag tggcggctgt ctaagaagtc tgaatctatc    2580
tgacaggagt atctgttacg tggccctcat acactgtaac atttctagaa ttcatggccc    2640
agctatagca gaataattta tttcagagtt aacctgaaac cacctgttgg aacgtcccac    2700
taatgctatc caggtgaagg gcttccctac ccctctgctc caccgctagt aaagccaaaa    2760
tacaccccct ctggatctcc ccatatccac ctctcccaaa tgcagacact gatgggtaat    2820
taacaccact gagaatccca gggtagaaat aaaggctcag tctctaaaca ctcaactcag    2880
atggagccac tgggtctaaa tgctcaccct gtggtttgtt ctcttgtaga tgccatctac    2940
gactgctctt ccctctacca gaagaactac cgcatctctg gagtgtataa gcttcctcct    3000
gatgacttcc tgggcagccc tgaactggag gtgaggtcat tacagtcact ggccatgccc    3060
taatacctgt ccttcacccc ctcaagggga ctacaacaac agggccattc acagtttaaa    3120
gaaaggaaaa ttcggctggg cgcagtggct cacacctgta atcccagcac tatgggaggc    3180
cgaggcaggt ggatcacttc aggtcaggag tttaagacca gcctggccaa catggtgaaa    3240
ccctgtctct actaaaaata caaaaaatt agccaggcat ggtggtgggc acctgtaatc    3300
cctgctacac aggaggattg cttgaactca ggaggcagag gttgcagtga gccgagatca    3360
cgccactgca ctataatctg ggagacaaag tgagactcca tttcaattaa aaaaaaaaa    3420 aaaaaaagg aaaactcaaa cacaagcaaa cacaccaaac accacagagc tatgcaaaca    3480
ctcagtttat gccctgcact ccaaacccag gcatctgttt ggcccccttca aatcattatc    3540 agtcaaacaa caagccttct aacatagatc agatcattct tataaccacc acataactta    3600
gtttaaatct cttgccatgt cctagaacag ctattccttg ggggaggaga aaagaaaaca    3660
cgaaggcagc atcaaattat ctggattttc acccaggcat ggtggctcac acctgtaatc    3720
ccaagttttt tgggaggtga ggtgggcgga acaatcacct gaggtcagga ctttgagacc    3780
agcctggcca acatgctgaa acccagtctc tactaaaaat acaaaaatta gcccagtgtg    3840
gtgacaggca ctctggtccc agctactagg aaggcaggag aatcactgga actcaggagg    3900
tggaggttgc agtgagccga gattgcacca ctgtactcta gcctgggcaa caagagtgaa    3960
attctgcttc aaaaaaaaaa aaagtatctg gattttccc tccaagcttc atgtgcactc    4020 accccgggc ccaatttgca tcgttcttcc agagcaatgc accacccacc ccagctcacc    4080
agcagtgggg cagcatcact gcccgagtga gccagtgtga ctgcgggagt gcacacatct    4140
actggctctg cagggacagg aacaggttgg gaagcctgcc ctcttgctcc tgccttctgc    4200
ccctgcaagt ccctcaccag agtatcccct ctgcttcagg tgttctgtga catggagact    4260
```

-continued

```
tcaggcggag gctggaccat catccagaga cgaaaaagtg gccttgtctc cttctaccgg    4320
gactggaagc agtacaagca gggctttggc agcatccgtg gggacttctg gctgggaac     4380 gaacacatcc accggctctc cagacagcca cccggctgc gtgtagagat ggaggtaagc     4440
acaaggccag gggcccatg actgaccag tgccaccaca catgaccgcg tacaactccg      4500
ggggtgccat tcctattctg attcaagaca aatctgtata ttcattgtga tggttttcct   4560
gcaagttgta atggagttga ggaaaaatag gtattttcc tttctgcaac ccccccaacc    4620
ccccgacaaa agtggggctg caggtgggac aggaagaggc cagacccagg ccagagtaga   4680
gcaaattcaa cagtcagctg tgccgaacac tagtctctgc tctggccgag catgaggtcc   4740
tttaggtgca atcttactg atactgtttg ggaccccttg ctgaaggtct gaaagcactc    4800
actatatcct catgttctc ttacagcagc tctgtgtggg attcagcaaa acatagctg     4860 caccttataa gcaggaaagt gaggaatata gaaagagaga ctaatcaagg ccatatggtg   4920
aatcaggaaa gaagttcgag ccttgttttc tgattcccag gttaacacag taaactggag   4980
gtaaacaagt aataaagtct tattagattc acacctataa aaagatgtttt ggctatggga  5040 ctgtcaggag agaaggggta tagagacagc atgaaatgga gcctgctgca ctttctttaa   5100
ggctctgctc ctcctgacag gactgggagg gcaacctgcg ctacgctgag tatagccact   5160 ttgtttggg caatgaactc aacagctatc gcctcttcct ggggaactac actggcaatg    5220
tggggaacga cgccctccag tatcataaca acacagcctt cagcaccaag gacaaggaca   5280
atgacaactg cttggacaag tgtgcacagc tccgcaaagg tgagatttgg ggggaccgga   5340
aaggagaagt tcaggtacaa gctcataatc ccacttgagg agaaagagtg aattataact   5400
gtacagttga tattccggtt ttggtattct ttctgaccct ggctctaact ccttacctga   5460
tgtctggtct atcacagtca acttactagc actgggtctg tttctcatgc caggtggcta   5520
ctggtacaac tgctgcacag actccaacct caatggagtg tactaccgcc tgggtgagca   5580
caataagcac ctggatggca tcacctggta tggctggcat ggatctacct actccctcaa   5640
acgggtggag atgaaaatcc gcccagaaga cttcaagcct taaaaggagg ctgccgtgga   5700
gcacggatac agaaactgag acacgtggag actggatgag ggcagatgag gacaggaaga   5760
gagtgttaga aagggtagga ctgagaaaca gcctataatc tccaaagaaa gaataagtct   5820
ccaaggagca caaaaaatc atatgtacca aggatgttac agtaaacagg atgaactatt     5880
taaacccact gggtcctgcc acatccttct caaggtggta gactgagtgg ggtctctctg   5940
cccaagatcc ctgacatagc agtagcttgt ctttccaca tgatttgtct gtgaaagaaa    6000
ataattttga gatcgtttta tctatttct ctacggctta ggctatgtga gggcaaaaca    6060
caaatccctt tgctaaaaag aaccatatta ttttgattct caaggatag gcctttgagt   6120 gttagagaaa ggagtgaagg aggcaggtgg gaaatggtat ttctattttt aaatccagtg   6180
aaattatctt gagtctacac attatttta aaacacaaaa attgttcggc tggaactgac    6240
ccaggctgga cttgcgggga ggaaactcca gggcactgca tctggcgatc agactctgag   6300 cactgccct gctcgccttg gtcatgtaca gcactgaaag gaatgaagca ccagcaggag    6360
gtggacagag tctctcatgg atgccggcac aaaactgcct taaaatattc atagttaata   6420
caggtatatc tatttttatt tactttgtaa gaaacaagct caaggagctt ccttttaaat   6480
tttgtctgta ggaaatggtt gaaaactgaa ggtagatggt gttatagtta ataataaatg   6540
ctgtaaataa gcatctcact ttgtaaaaat aaaatattgt ggttttgttt taaacattca   6600
```

```
acgtttcttt tccttctaca ataaacactt tcaaaatgtg a                6641
```

<210> SEQ ID NO 14
<211> LENGTH: 346
<212> TYPE: PRT
<213> ORGANISM: Homo sapiens

<400> SEQUENCE: 14

```
Met Leu Lys Lys Pro Leu Ser Ala Val Thr Trp Leu Cys Ile Phe Ile
1               5                   10                  15

Val Ala Phe Val Ser His Pro Ala Trp Leu Gln Lys Leu Ser Lys His
                20                  25                  30

Lys Thr Pro Ala Gln Pro Gln Leu Lys Ala Ala Asn Cys Cys Glu Glu
            35                  40                  45

Val Lys Glu Leu Lys Ala Gln Val Ala Asn Leu Ser Ser Leu Leu Ser
        50                  55                  60

Glu Leu Asn Lys Lys Gln Glu Arg Asp Trp Val Ser Val Val Met Gln
65                  70                  75                  80

Val Met Glu Leu Glu Ser Asn Ser Lys Arg Met Glu Ser Arg Leu Thr
                85                  90                  95

Asp Ala Glu Ser Lys Tyr Ser Glu Met Asn Asn Gln Ile Asp Ile Met
            100                 105                 110

Gln Leu Gln Ala Ala Gln Thr Val Thr Gln Thr Ser Ala Asp Ala Ile
        115                 120                 125

Tyr Asp Cys Ser Ser Leu Tyr Gln Lys Asn Tyr Arg Ile Ser Gly Val
    130                 135                 140

Tyr Lys Leu Pro Pro Asp Asp Phe Leu Gly Ser Pro Glu Leu Glu Val
145                 150                 155                 160

Phe Cys Asp Met Glu Thr Ser Gly Gly Gly Trp Thr Ile Ile Gln Arg
                165                 170                 175

Arg Lys Ser Gly Leu Val Ser Phe Tyr Arg Asp Trp Lys Gln Tyr Lys
            180                 185                 190

Gln Gly Phe Gly Ser Ile Arg Gly Asp Phe Trp Leu Gly Asn Glu His
        195                 200                 205

Ile His Arg Leu Ser Arg Gln Pro Thr Arg Leu Arg Val Glu Met Glu
    210                 215                 220

Asp Trp Glu Gly Asn Leu Arg Tyr Ala Glu Tyr Ser His Phe Val Leu
225                 230                 235                 240

Gly Asn Glu Leu Asn Ser Tyr Arg Leu Phe Leu Gly Asn Tyr Thr Gly
                245                 250                 255

Asn Val Gly Asn Asp Ala Leu Gln Tyr His Asn Asn Thr Ala Phe Ser
            260                 265                 270

Thr Lys Asp Lys Asp Asn Asp Asn Cys Leu Asp Lys Cys Ala Gln Leu
        275                 280                 285

Arg Lys Gly Gly Tyr Trp Tyr Asn Cys Cys Thr Asp Ser Asn Leu Asn
    290                 295                 300

Gly Val Tyr Tyr Arg Leu Gly Glu His Asn Lys His Leu Asp Gly Ile
305                 310                 315                 320

Thr Trp Tyr Gly Trp His Gly Ser Thr Tyr Ser Leu Lys Arg Val Glu
                325                 330                 335

Met Lys Ile Arg Pro Glu Asp Phe Lys Pro
            340                 345
```

<210> SEQ ID NO 15
<211> LENGTH: 5183

<212> TYPE: DNA
<213> ORGANISM: Mus musculus

<400> SEQUENCE: 15

```
tcagactaag gaaggaaaga gttccatttc agaatctcta gctttaagaa aggctaagca      60
agcacacaga ggaaggagat cacggggaag aagaaaact gccagtgtgg gtcagagaaa      120
gaagcttcct acttctccag ggacagactc taaggggaac aggcctgcac accatgctga     180
gggagacctg gctatgtgtt atccttgtag cctttgtcag ccacccagtg tggctgcaga     240
agcctcataa acgcaagaca cagctcaaag cagcgggctg ctgtgaggag atgagggagc     300
tcaaagccca ggtggccaac ctcagcagtc tgctgggaga gctgagcagg aagcaggaga    360
gcgactgggt cagtgtggtc atgcaggtga tggagctgga gagcagcagc aagcacatgg    420
agtctcggct cagcactgcc gagagcaagt actctgagat gaacaaccag attgacatca    480
tgcagctgca ggctgcgcag accgtcacgc agacctcggc aggtaagtgc tgcctccaca    540
ctcctcaccg tgcgcctgct caaggtctcc tggccccagc tctgcttctg gatagcctgc    600
tcaacaactt cgggggcttt tgggaatgta cgatctatga ttgcacaagc tttgggctag    660
tgatatcctg cgagtttagc caggacattt gaagaaaacc tttgtattca acaaaggaca    720
gactcctcgt gttcttcaat tctgatcttc tttctcccat ggtggctaat aaaattcttc    780
caaataatag agaacaag taatgtaat gctgaagtgc tgacctttta gtggctgaaa    840
ataaggaagg cacacgcagt gagttatttg agaaaaaaac attcagttgt tggttaactt    900
ggcacagatg agctaataaa tgaatcgctg ctcagatgaa gatctaattt tctgaggtta    960
ctggaaaaca tttggagtaa gtatatttta tagatgaagc atttcttact aatgcttact   1020
gcacaataaa ccaagtcaag aagacatgat tagcttcttg tgagtaagac cttggctatc   1080
attggttcag acaaagaaaa agttttgctg aaagttaagc ctgaaaagtc tgttagctaa   1140
ttaaacaaaa acaaatgatt tcagagcttg ggcctcctga ccctcagttt gaaaacagaa   1200
agttagggt tctcatttac caaaggagg gagagagaga gagtgtgtgt gttcatttgt   1260
tctgtgagat ggaactggtc atgttggcca ggccagatgc acgcagggct gactgtacca   1320
cttcttgctc ctagaagtcg gctgggagga agggcaggta tcctcattcc tccccccccc   1380
cccccccccc agcacgctct gcagaggaaa taggcacttt ggcatctccc actttcatct   1440
atgctcccta agtctccagc caaggggcac caaggaaaaa gtctcaagac atgcagaagt   1500
gtcttgggc aacagccaca gagtctgcta aaaacagctg cttctttgaa gccccaggac   1560
agagcctcaa ggcggccatg gaagctttca gatcaagccc aaggggaagt ggggaaactt   1620
cacttcctgg atttttaaa aagaattatt tattattata cataagtaca ctgttgctgt   1680
cttcagatgc accagaagag gggagtcagat cttattatgg gtggttgtga gctaccatgt   1740
ggttgctggg atttgaactc aggaccttcg gaagagcagt cagtgctctt actcgctgag   1800
ccatctcgcc agccccactt ccttgattta tcaaagtttt aggaacagtc tcaagtgctg   1860
ctggttttca tttgagcatc tagtgatgtg agactgggga gggagaagat ttccaatctg   1920
tctcccttaa tctgagtacc tgttggctgg tagctgagaa acaacataaa accaaactcc   1980
ctgaaatact ctggagtttg cctctagctc aagcctgaag cttctctcag ggcagctgcc   2040
acgtgcccct tcgcagacca t accattattg tttctggaat tcacagcctg gcacttcagc   2100
aggatgtctt acttagactt agcccgaagc ttcctgctta acgtccctt ggcacaggtt   2160
aagaatcccc ttactctact gccccataac caaggcgggcc tgagcaggcc tctcagccct   2220
```

```
gatgcccact tctcgacatc ggtaccccag gggaactacc cacgggcacg ctgaggtaca    2280
aatcaagtct tggtttttaa tccagctcag atgcaccagg catgtctgac caacctcaag    2340
gcccaaatct ctgtttactc tgcgtccctc acagatgcca tctatgactg ttcttccctg    2400
taccagaaga actaccgaat ctctggagtg tacaagcttc ctcctgacga gttcctgggg    2460
agccctgagc tagaggtgag gtcactactg ccctgcccta cccttttgtcc tccagccctg    2520 aaaggtacat ggataacagg acttcttctg gtctatggaa agggaagttc aagaatcaaa    2580
tgtaccccat gatggactgt gagaatgctc agtttacggg cccctccctc cactccagcc    2640
cgctactgtc tgcagaatca gctgtcctag ttcttcccga cacagaacga gatcagctct    2700
ctctaggagg agggaagaca ctagaaggag acacgtggaa gtacctgatt ttcccattta    2760
cattgtgttc acactgcctg cccgccatgc cccactgaca ctcgttccca agctagccac    2820
caccgtgccc ccgcctccac gttgggggca gtgtttctgc tagagaatgc agagagcaca    2880
aggatcactg actcactaga tagatacagc acacagcttg ggaagtctgt ccttaagctc    2940
ctgcccctgc ccttgcgcct gcccagaggg tcctctctgc ttcaggtgtt ctgtgacatg    3000
gaaacttcag gaggaggctg gaccatcatc cagagacgta agagtggcct tgtctccttc    3060
taccaagact ggagacagta taagcaaggg tttggcagca tccgaggtga cttctggctg    3120
gggaatgaac atatccaccg gctcaccagg cagccaagcc ggcttcgtgt ggagctggag    3180
gtaagctcga gctgcaaggc cccgtctggc ccaggcccac tgcacacatg ttcataggc    3240 atcaccacag tctactcact ctaggtgtgc tcagtcagtg cagcaatgct cctgaaagct    3300
ttctgttttt ctgtctccaa gcgaggtcca ggaagaccca gggcagaaca gggtaaatgc    3360
atagttactg ggatggaaag aaaacaccat ctcctttgct ctgggatctt gttaagtaca    3420
agccacagtg atgctgtgtg gtggcccctt tagatggctt caagcatgat gtcctcactt    3480
actcctaccg catctcagga tgagatttaa cacaaaccac acatctgccc cttcagacag    3540
acatgaaggg ttgcagacaa gcaatccagg ccatacggtg agaccagacc caagtttgct    3600
ctcagacctt cgtttgctga ctgctagcta acatggcaac ctgcaatagt cttaccagag    3660
ttccacctct gaagaaatgt ttagccgtgg cgctcatgag agaggaaggg accgaggtct    3720
gcagaaacga atcctttatg gtttccctaa tgctctgctc ctccttttca ggactgggag    3780
ggcaatgcac gctacgcaga gtatagctac tttgcgttgg gcaatgaact gaacagctac    3840
cgcctcttcc tgggaactac cagtggcaac gtggggaagg acgccctcct ctaccataac    3900
aacaccgtct tcagcaccaa ggacaaggac aacgacaact gcttggacaa gtgcgcacag    3960
ctccgaaaag gtgagacctg ggcggcaggg agggctgggc ccactaagga cagcagtgag    4020
ctacagatct gttgctgctg ctctggccgt gctgtcccct tcgctttaag gccacccatc    4080
agccctagtc tagggaggac gtccccagcc tactagcctc atctgtctct catgccaggt    4140
ggctactggt acaactgctg cacagactcc aacctcaatg gggtgtacta ccgccttggc    4200
gagcaccgaa agcacatgga tggcatcagc tggtatggct ggcatggagc caactattcc    4260
ctcaaacgtg tggaaatgaa gatccgccca gaagccttca gccctgaga gaaggcagac    4320 actgaggagg gagaacagca tgggaggagg aggtggacac agggtaggag ggaacagttt    4380
atcatccagg agcacaatat aactttacct gtgtgagcac acacacacaa tagaaccaca    4440
cgtgccaaca gtgcacacta gcagatggag ccaggcggac ccagtggggc ctgccacggt    4500
gcctcacggg agaactcatg gacaacggta accctgaggt cacttaaccc attttcccta    4560
actgaggctt agatgacacg agggaaaaga acaaataaaa acctggtgtg attctcagcg    4620
```

```
gagaggctgt gagaaatgaa agaaagcagg tggtggagaa ggggcttcca agtcttaccc    4680
cgcgacactt ccttgtgtct atagtatttg ttttgttttt cttttgaga cagggtctct    4740 ctacacagct ctttctgtcc tggaactcac tatgtagacc aggctgacct tgaactcaca    4800
gagatctacc tgcttctgcc tcccaagtac agggattaaa ggcatgtacc accataccca    4860
gtatatataa ttttaagac acaaaaaaca tggagataga gagcagctgc ccaggtgtct    4920 ccggggggc cttgttgtca gagtcctggg ggagagagga gcactggaca acatgctgcg    4980
ggtctgacgt ggcgagaaca ccagccggag gtgagcacag actctgggtg atcacaatac    5040
tgccttcaaa catcctcagt caaaaaccaa aagatcccct ttaataaaaa tgcttggaaa    5100
atgaaggtag atggcgctgt ggtttaaaac ttgtgatgta tatagaagca tcttccttgt    5160
aaaaataaaa tattgtaatt cct                                           5183
```

<210> SEQ ID NO 16
<211> LENGTH: 337
<212> TYPE: PRT
<213> ORGANISM: Mus musculus

<400> SEQUENCE: 16

```
Met Leu Arg Glu Thr Trp Leu Cys Val Ile Leu Val Ala Phe Val Ser
1               5                   10                  15

His Pro Val Trp Leu Gln Lys Pro His Lys Arg Lys Thr Gln Leu Lys
            20                  25                  30

Ala Ala Gly Cys Cys Glu Glu Met Arg Glu Leu Lys Ala Gln Val Ala
        35                  40                  45

Asn Leu Ser Ser Leu Leu Gly Glu Leu Ser Arg Lys Gln Glu Ser Asp
    50                  55                  60

Trp Val Ser Val Val Met Gln Val Met Glu Leu Glu Ser Ser Ser Lys
65                  70                  75                  80

His Met Glu Ser Arg Leu Ser Thr Ala Glu Ser Lys Tyr Ser Glu Met
                85                  90                  95

Asn Asn Gln Ile Asp Ile Met Gln Leu Gln Ala Ala Gln Thr Val Thr
            100                 105                 110

Gln Thr Ser Ala Asp Ala Ile Tyr Asp Cys Ser Ser Leu Tyr Gln Lys
        115                 120                 125

Asn Tyr Arg Ile Ser Gly Val Tyr Lys Leu Pro Pro Asp Glu Phe Leu
    130                 135                 140

Gly Ser Pro Glu Leu Glu Val Phe Cys Asp Met Glu Thr Ser Gly Gly
145                 150                 155                 160

Gly Trp Thr Ile Ile Gln Arg Arg Lys Ser Gly Leu Val Ser Phe Tyr
                165                 170                 175

Gln Asp Trp Arg Gln Tyr Lys Gln Gly Phe Gly Ser Ile Arg Gly Asp
            180                 185                 190

Phe Trp Leu Gly Asn Glu His Ile His Arg Leu Thr Arg Gln Pro Ser
        195                 200                 205

Arg Leu Arg Val Glu Leu Glu Asp Trp Glu Gly Asn Ala Arg Tyr Ala
    210                 215                 220

Glu Tyr Ser Tyr Phe Ala Leu Gly Asn Glu Leu Asn Ser Tyr Arg Leu
225                 230                 235                 240

Phe Leu Gly Asn Tyr Ser Gly Asn Val Gly Lys Asp Ala Leu Leu Tyr
                245                 250                 255

His Asn Asn Thr Val Phe Ser Thr Lys Asp Lys Asp Asn Asp Asn Cys
            260                 265                 270
```

Leu Asp Lys Cys Ala Gln Leu Arg Lys Gly Gly Tyr Trp Tyr Asn Cys
            275                 280                 285

Cys Thr Asp Ser Asn Leu Asn Gly Val Tyr Tyr Arg Leu Gly Glu His
        290                 295                 300

Arg Lys His Met Asp Gly Ile Ser Trp Tyr Gly Trp His Gly Ala Asn
305                 310                 315                 320

Tyr Ser Leu Lys Arg Val Glu Met Lys Ile Arg Pro Glu Ala Phe Lys
                325                 330                 335

Pro

<210> SEQ ID NO 17
<211> LENGTH: 3919
<212> TYPE: DNA
<213> ORGANISM: Rattus norvegicus

<400> SEQUENCE: 17

| | | | | | |
|---|---|---|---|---|---|
| cacacaatgc | tgaggaccac | ctggctatgc | attctcctgg | tagcctctgt | cagtcgcccc | 60 |
| gtgtggctgc | agaagcctca | taaacgcaag | acacagctca | agcagccgg | ctgctgtgag | 120 |
| gagatgaggg | agctcaaggc | ccaggtcgcc | aacctcagca | gtctgctggg | tgagctgagc | 180 |
| aggaagcagg | agagcgactg | ggtcagtgtg | gtcatgcagg | tgatggagct | ggagagcagc | 240 |
| agcaagcgca | tggagtctcg | gctcaccact | gccgagagca | agtactctga | gatgaacaac | 300 |
| cagatcgaca | tcatgcagtt | acaggctgca | cagaccgtca | cacagacctc | ggcaggtaag | 360 |
| cgctgtcccc | acactcctcc | ctcaccatgc | tcctgctaag | tctcctggtt | ccagtctgct | 420 |
| tctggattgc | ccactcagca | caactctggg | gggcttttgg | ggatgcacca | tctttgtttg | 480 |
| ggttagtgat | gtcctgtaag | cttagccagg | atatcacagc | ctgtagccat | ttgaagaaaa | 540 |
| cctttgtatt | caacaaagga | cagacacttg | gtgctgtaca | gttctgatcc | actttctccc | 600 |
| atgattgcta | gtacagctct | cccaaataac | agagagaaca | atgaaggtgc | tgctgaagtg | 660 |
| ctgacttcag | tggctgaaaa | taaggaaggc | acacacagtg | agttctcggg | aaaacaacag | 720 |
| tcagttgctg | ggtaacctgg | cccagatgag | ccaagagatg | aattgctgct | cagagaaaga | 780 |
| tctaattttc | tgaggttact | ggaaaacatt | tggaatgatt | atattttata | gatgaagcat | 840 |
| ttcttactaa | tgcttactgc | acaataaccc | aagtcaagaa | gacatgatta | gctcctattg | 900 |
| agtaagacct | ggctacccctt | ggttcagaca | agaagaagt | tttgcccaag | gtagctggtt | 960 |
| aaacaaatac | aaatgatttc | aaagcgtagt | tctcctgacc | tcggtttgag | aacagaaagt | 1020 |
| tagggggttct | catttaccaa | aaaagtgagt | ctttatttgc | tctgtgagat | gaaaatggtc | 1080 |
| atgtaaacca | ggccagacgc | agggctgact | gcaccacttc | ttgctcctag | aagtcgcagg | 1140 |
| aggaagggca | ggtatagcac | attcccctttt | cccagcatgc | tctgctgagg | ggacaggcac | 1200 |
| tttggaatct | cccactttca | cctgtgcttt | ccctaagcc | tccagcccag | ggggcaccaa | 1260 |
| ggaaaaagtc | ccaagacaag | tgcagaagta | tcctgtggac | aacagccaca | gactctacta | 1320 |
| caaacagctg | cgtctttgaa | gcctcagtac | aaagcagcag | ctgcaaggca | gccacagacg | 1380 |
| ctttcaaatc | aagcccaagg | ggaagtggga | aaacctcatt | accttgattt | atcaaaactt | 1440 |
| tcagggaaca | gtctcaaagg | gctgcttgga | gttttggttt | tcatttgaac | gtctagtgat | 1500 |
| gtgagattgg | ggagggataa | gattcaaatc | tgtctcccctt | aatttgagta | cctgttggct | 1560 |
| gttagctgag | aaacaccacc | aaaccaaact | ccccgagata | tcaggagtt | ggcctctagc | 1620 |
| tgaggtctga | ctcaagaagt | ctgaagcttc | tcctagggta | gctgccaagt | ggcctttgca | 1680 |

```
gaccatccta ttactgtttc cagaatttac agcctagcac cacaacagga tgtcctatat    1740
agacttagcc tgaagcttcc tgcttaatgg tgccttggca caggtaaaga gtttccttac    1800
tctatggcct cataaccaag gaagcccaaa catccccctc ggtcctgatg cacttcttga    1860
actcgatacc tcgggggaac tacccacagg caccatgggc agaaataaag tctcggtttt    1920
gaacccagct cagatgcagc agacatgccc ccccaaactc aaggcctgaa tctctgtcca    1980
ctctgttccc ctcacagatg ccatctacga ctgttcctcc ctgtaccaga agaactaccg    2040
aatctctgga gtgtacaagc ttcctccaga tgagttcctg ggcagccctg agttagaggt    2100
gaggtcaaca gtgccatgtc ctactctttg tcctccacct taaaaggcac agtgacaaca    2160
ggacaaccct ggtctacaga aagggaaatt ctaaaaagca aacgtgccct atgatggagc    2220
tgtgagaagc tcaatttatg gggctctgcc tctattccgc cctccgttgg cagagtatca    2280
gtcagacatc gactgtccca gttcttgcga cacagaatga gttcagatct ctctctagga    2340
gaggagagaa gtcattagga ggagacacac agaagtacct catttcccac ttacgctgtg    2400
ttcacactgc ccgccctgcc ccaggtacac tcattcccaa ggtaaccatt gtgcccttgg    2460
ccctccacac tgggggcagt gtctctgctg gattatgcag ggagcacaag gaccactaac    2520
acaacaggta cagcacatag gtttggaagt ctgtccttaa gctcctgccc ctgcccttgc    2580
acctgcccag aggatccttt ctgctttagg tgttctgtga catggaaact tcaggaggag    2640 gctgaccat catccagagg cgcaagagtg gcctagtctc cttctaccaa gactggaaac    2700
agtataagca agggtttggc agcattcgag gcgacttctg gctagggaat gaacatattc    2760
accggcttac caggcagcca acaaggcttc gtgtggagct ggaggtaagc ttgagctgta    2820
aggcctgact ggcccaggcc tactgcacac agggttcaga ggcatcgcca cagtctgctc    2880
acttcaggtg tgcagagtca gggcagcagt gtccctggac agtttatttc tatctctaag    2940
caaaactgaa ctgcagctga ccgaggtcca ggaagaccca tagcgactgg gatggaaaca    3000
ccatctcctt tgctctgcga tcttgttaag tacaagcctc actggggctg cgtggtggcc    3060
cctttagctg gcttcaagca cgatgccagc ctacttactc ctacagcatc tcagagtgag    3120
atttaacaaa aatcacacat ctgcccctc agacagaggc atgaagggtt acagacagaa    3180
cgatccaggc cacatggacc cagacccaag tttggtctca gacctttcta tgctgacttc    3240
tagctaacat ggcaacctgt aatagtctta ccagagttcc acctctgaag agaggtttag    3300
ctgcggggct agtgagtgag gaaaggatgg ggtctgcagc aatgaagtcc tctgtggttt    3360
ccctaaggct ctgctcttcc ttggcaggac tgggagggca acgcacgcta cgcagagtac    3420
agctactttg cgttgggcaa tgaactgaac agctaccgcc tcttcctggg gaactacagt    3480
ggcaacgtgg ggaaggacgc tctcctctat cataacaaca ccgtcttcag caccaaggac    3540
aaggacaatg acaactgctt ggacaagtgt gcacagctcc gaaaaggtga gacctgggag    3600 gcagggagg gctgggtcca ctaaggacag cagtgagctg tagatttgct gcaggtgctc    3660
tggctgtgct gtctcctttg ctttaacgcc atcaatcagc cagaatctag ggagggcatc    3720
cccagcctac tagctgtgtc tcacgccagg tggctactgg tacaactgct gcacagactc    3780
caacctcaat ggggtgtact accgcctggg ggagcaccgg aagcacatgg atggcatcag    3840
ctggtatggc tggcatggag ccaactattc cctcaaacgg gtggagatga agatccgtcc    3900
agaagccttc acgccctag                                                 3919
```

<210> SEQ ID NO 18
<211> LENGTH: 337

<212> TYPE: PRT
<213> ORGANISM: Rattus norvegicus

<400> SEQUENCE: 18

```
Met Leu Arg Thr Thr Trp Leu Cys Ile Leu Leu Val Ala Ser Val Ser
1               5                   10                  15

Arg Pro Val Trp Leu Gln Lys Pro His Lys Arg Lys Thr Gln Leu Lys
                20                  25                  30

Ala Ala Gly Cys Cys Glu Glu Met Arg Glu Leu Lys Ala Gln Val Ala
            35                  40                  45

Asn Leu Ser Ser Leu Leu Gly Glu Leu Ser Arg Lys Gln Glu Ser Asp
        50                  55                  60

Trp Val Ser Val Val Met Gln Val Met Glu Leu Glu Ser Ser Ser Lys
65                  70                  75                  80

Arg Met Glu Ser Arg Leu Thr Thr Ala Glu Ser Lys Tyr Ser Glu Met
                85                  90                  95

Asn Asn Gln Ile Asp Ile Met Gln Leu Gln Ala Ala Gln Thr Val Thr
                100                 105                 110

Gln Thr Ser Ala Asp Ala Ile Tyr Asp Cys Ser Ser Leu Tyr Gln Lys
            115                 120                 125

Asn Tyr Arg Ile Ser Gly Val Tyr Lys Leu Pro Pro Asp Glu Phe Leu
        130                 135                 140

Gly Ser Pro Glu Leu Glu Val Phe Cys Asp Met Glu Thr Ser Gly Gly
145                 150                 155                 160

Gly Trp Thr Ile Ile Gln Arg Arg Lys Ser Gly Leu Val Ser Phe Tyr
                165                 170                 175

Gln Asp Trp Lys Gln Tyr Lys Gln Gly Phe Gly Ser Ile Arg Gly Asp
                180                 185                 190

Phe Trp Leu Gly Asn Glu His Ile His Arg Leu Thr Arg Gln Pro Thr
            195                 200                 205

Arg Leu Arg Val Glu Leu Glu Asp Trp Glu Gly Asn Ala Arg Tyr Ala
210                 215                 220

Glu Tyr Ser Tyr Phe Ala Leu Gly Asn Glu Leu Asn Ser Tyr Arg Leu
225                 230                 235                 240

Phe Leu Gly Asn Tyr Ser Gly Asn Val Gly Lys Asp Ala Leu Leu Tyr
                245                 250                 255

His Asn Asn Thr Val Phe Ser Thr Lys Asp Lys Asp Asn Asp Asn Cys
                260                 265                 270

Leu Asp Lys Cys Ala Gln Leu Arg Lys Gly Gly Tyr Trp Tyr Asn Cys
            275                 280                 285

Cys Thr Asp Ser Asn Leu Asn Gly Val Tyr Tyr Arg Leu Gly Glu His
290                 295                 300

Arg Lys His Met Asp Gly Ile Ser Trp Tyr Gly Trp His Gly Ala Asn
305                 310                 315                 320

Tyr Ser Leu Lys Arg Val Glu Met Lys Ile Arg Pro Glu Ala Phe Thr
                325                 330                 335

Pro
```

BIOMARKERS FOR DETERMINATION OF TEMPORAL PHASE OF ACUTE KIDNEY INJURY

CROSS-REFERENCE TO RELATED APPLICATIONS

This is the U.S. national stage of International application PCT/EP2011/060125, filed Jun. 17, 2011 designating the United States and claiming the benefit of U.S. provisional application 61/355,723 and claiming priority to EP 10075261.7, both filed Jun. 17, 2010.

SEQUENCE LISTING

The instant application contains a Sequence Listing, which has been submitted via EFS-Web and is hereby incorporated by reference in its entirety. Said ASCII copy, created on Dec. 17, 2012 is named eolf-othd-000001.txt and is 87181 bytes in size.

The invention relates to a method for determining the temporal phase of acute kidney injury, comprising obtaining a test sample from a subject and measuring the expression level of at least one biomarker selected from the group comprising Chac1, Birc5 and Angptl7. The invention also relates to a method for determining the early early phase, the late early phase, the severity and/or timing of acute kidney injury via analysis of the biomarkers Chac1, Birc5 and/or Angptl7, in addition to a test kit for carrying out said methods and antibodies directed against Chac1, Birc5 or Angptl7.

BACKGROUND OF THE INVENTION

Renal injuries or disease, such as acute kidney failure or chronic kidney failure, can result from a variety of different causes (such as illness, injury, and the like).

Acute kidney injury (AKI) is a rapid loss of kidney function. AKI is so far diagnosed on the basis of clinical history, like decreased urine production, elevated blood urea nitrogen and creatinine. AKI can lead to numerous complications, including metabolic acidosis, high potassium levels, changes in body fluid balance, and effects to other organ systems. AKI is observed in 5% of hospitalized patients and associated with a high mortality.

The molecular mechanisms of tubular regeneration after ischemic renal injury remain largely unknown. An understanding of the mechanisms that lead to renal cell proliferation and regeneration will be necessary for the exploration of novel therapeutic strategies for the treatment of ischemic AKI. Some reports have proposed that regeneration processes may recapitulate developmental processes to restore organ or tissue function. The adult tubular epithelial cells have a potent ability to regenerate after cellular damage. Under a condition of ischemic renal damage, normally quiescent cells undergo dedifferentiation and acquire the ability to proliferate after their DNA synthesis is enhanced.

AKI begins by inducing molecular modifications later evolving into cellular damage. The cells start producing markers of injury and the clinical syndrome develops subsequently. Biomarker expression represents an earlier stage in progression to clinical syndrome (Ronco et al., 2008). Thus, detection of biomarkers may provide the much needed window of opportunity for early intervention. Based on the differential expression of the biomarkers, it is also likely that the biomarker panels will distinguish between the various types and etiologies of AKI. Possible newer biomarkers of AKI can be components of serum or urine or can be imaging studies or any other quantifiable parameter. New biomarkers are likely to be useful in facilitating early diagnosis, guiding targeted intervention and monitoring disease progression and resolution.

The early identification and treatment of renal injuries and disease would be useful in preventing disease progression. Currently, serum creatinine is frequently used as a biomarker of kidney function. However, serum creatinine measurements are influenced by muscle mass, gender, race and medications. Unfortunately, these limitations often result in the diagnosis of kidney disease only after significant damage has already occurred.

The diagnosis and prognosis of acute kidney injury (AKI) by current clinical means is inadequate (Parikh et al., Ann Clin Biochem 2010; 47: 301-312). In an effort to enhance diagnosis, biomarkers for the early detection of acute kidney injury have recently been introduced into clinical practice. These biomarkers, such as NGAL (Mishra et al., J Am Soc Nephrology, vol. 14, 2003) or Kim-1, can be detected in urine, serum or kidney biopsies and, when levels of the biomarkers are elevated, allow acute kidney injury detection within 2-4 hours of the precipitating event (e. g. surgery, shock, sepsis, nephrotoxin administration). In this regard, the newly introduced biomarkers (e. g. NGAL, Kim-1) outperform conventional biomarkers (e. g. serum creatinine, blood urea nitrogen), which are elevated only later in the course of kidney injury. However, both the conventional and newly introduced biomarkers known in the art at the present time exhibit the significant disadvantage, that their expression is elevated for an extended time after acute kidney injury (in some cases more than 7 days after injury). Recent studies outline that NGAL for example is still strongly expressed long after injury (Krawczeski, et al, 2011, Journal of Pediatrics, 158(6): 1009), in some cases more than 120 hours after injury (Mishra et al., Lancet 2005; 365: 1231-38).

Therefore, the biomarkers currently available exhibit expression profiles that enable identification that acute kidney injury has occurred at some point in the past, but allow neither a precise estimate of the time point of the precipitating event nor estimation or determination of the temporal stage of kidney regeneration. Large-scale approaches have been published, in which a number of genes or proteins are disclosed as being relevant biomarkers for detection of kidney injury, albeit only for detection of injury. Sufficient detail on the conciseness of expression profiles and their relation to the temporal phase of injury or regeneration in order to provide an accurate determination of injury time is not provided (WO 2009/083950 A2, WO 2009/127644 A1). Other biomarkers for AKI such as Keratinocyte-derived chemokine (Molls et al., Am J Physiol Renal Physiol 290:F1187-F1193, 2006) also show expression long after injury, thereby preventing use of such markers for determination of injury time or temporal phase after injury.

The biomarkers of the present invention relate to Chac1, Birc5 and Angptl7. Chac1 has been disclosed as useful in identifying substances that are active in preventing or treating a disease associated with a malfunction of carbohydrate or lipid metabolism (WO 2006/094735 A1) and has not previously been related to kidney disease. Birc5 has been implicated in kidney regeneration (WO 2006/051075 A1) and prevention of apoptosis in kidneys (Kindt et al., FASEB J. 2008 February; 22(2):510-21), although no mention has been made of Birc5 as a biomarker with the specific properties disclosed herein. Angptl7 has until now only been disclosed in relation to expression in human eyes in glaucoma patients (Kuchtey et al., IOVS, vo. 49, no. 8, 2008, Peek et al., Invest. Opthalmology & Vis. Science, vol. 39, no. 10, 1998). The inventive properties of the biomarkers of the present invention, which enable the method of the present invention, have been neither suggested nor disclosed by the prior art.

Known biomarkers, such as NGAL, can be seen as useful and early indicators for kidney injury, which remain present for very long times after injury. The biomarkers of the present invention and their use in a method of determining temporal phase, enable, in light of the known markers, the determination of more specific phases of injury and regeneration within the broad window of NGAL or creatinine expression.

In clinical practice, the time point of the precipitating event is frequently unknown. Hence, there is a need for biomarkers that allow a precise determination of the time point of acute kidney injury and facilitate a temporal staging of the disease.

SUMMARY OF THE INVENTION

In light of the prior art, the technical problem underlying the present invention is to provide biomarkers capable of determining the temporal phase of acute kidney injury.

This problem is solved by the features of the independent claims. Preferred embodiments of the present invention are provided by the dependent claims.

Therefore, an object of the invention is to provide a method for determining the temporal phase of acute kidney injury, comprising
  a) obtaining a test sample from a subject;
  b) determining the expression level of at least one biomarker selected from the group comprising Chac1, Birc5 and Angptl7.

The invention also relates to a method for determining the early early phase, the late early phase, the severity and/or timing of acute kidney injury, comprising
  a) obtaining a test sample from a subject;
  b) determining the expression level of at least one biomarker selected from the group comprising Chac1, Birc5 and Angptl7.

In a preferred embodiment the method as described herein is characterized in that the test sample is a urine, tissue or blood sample.

In a preferred embodiment the method as described herein is characterized in that DNA, RNA and/or protein is analyzed in the test sample.

In one embodiment the method as described herein is characterized in that the method is adapted for use in an automated system and/or semi-automated system.

In one embodiment the method as described herein is characterized in that said acute kidney injury comprises an injury selected from the group consisting of a renal tubular cell injury, ischemic renal injury, a nephrotoxic injury, and any other injury that affects the tubular cells of the kidney.

In one embodiment the method as described herein is characterized in that one or more other biomarkers, preferably creatinine, neutrophil gelatinase-associated lipocalin (NGAL), interleukin 18 (IL-18), kidney injury molecule 1 (Kim-1) and/or Liver fatty acid binding protein (LFABP) are analyzed before and/or in combination with analysis of Chac1, Birc5 and/or Angptl7.

In a preferred embodiment the method as described herein is characterized in that the subject exhibits a positive result for one or more of the biomarkers as provided in the preceding claim.

The invention also relates to a method as described herein characterized in that Chac1, Birc5 and/or Angptl7 is used for detecting the severity of acute kidney injury, preferably the severity of the early early phase or the late early phase, and/or as a therapy-accompanying or follow-up control biomarker.

The method of the present invention is in a preferred embodiment characterized in that Chac1 is selectively expressed in the early early stage of acute kidney injury.

The method of the present invention is in a preferred embodiment characterized in that Angptl7 is selectively expressed in the early early stage of acute kidney injury.

The method of the present invention is in a preferred embodiment characterized in that Birc5 is selectively expressed in the late early stage of acute kidney injury.

The present invention further relates to a method as described herein characterized in that Chac1, Birc5 and/or Angptl7 are used as biomarkers in the detection, diagnosis and/or follow-up control of the temporal phase of acute kidney injury in a subject, comprising:
  a) Determination of Chac1, Birc5 and/or Angptl7 expression level in a test sample obtained from a subject,
  b) Comparison of Chac1, Birc5 and/or Angptl7 expression in said test sample with a control sample, and
  c) Determination of the temporal phase of acute kidney injury based on the comparison in step b)
  whereby
  d) elevated levels of Chac1 and/or Angptl7 expression in said test sample in comparison to a control sample indicates the early early stage of acute kidney injury, and
  e) elevated levels of Birc5 expression in said test sample in comparison to the control sample indicates the late early stage of acute kidney injury.

The invention also relates to a test kit for carrying out the method according to any one of the preceding claims, comprising detection means that recognize Chac1, Birc5 and/or Angptl7 DNA, RNA and/or protein specifically, such as primer oligonucleotides or antibodies, and one or more containers and/or means for collecting and/or storing the sample to be analysed.

In a preferred embodiment the test kit of the present invention is characterized in that the kit contains additionally further means for carrying out procedures relating to an adapted use of the method in an automated system and/or semi-automated system.

The invention also relates to the use of Chac1, Birc5 and/or Angptl7 as a biomarker for determining the temporal phase of acute kidney injury, especially for determining the early early phase, the late early phase, the severity and/or timing of acute kidney injury.

The invention also relates to one or more antibodies that bind to Chac1, Birc5 or Angptl7 protein for use in determining the temporal phase of acute kidney injury, especially for determining the early early phase, the late early phase, the severity and/or timing of acute kidney injury.

The invention also relates to the use of one or more antibodies that bind to Chac1, Birc5 or Angptl7 for determining the temporal phase of acute kidney injury, especially for determining the early early phase, the late early phase, the severity and/or timing of acute kidney injury.

The present invention demonstrates the surprising advantage that quantitative analyses of these biomarkers (e. g. in tissue, such as kidney biopsies, urine or blood) can be used for diagnostic tests for the determination of the time point of kidney injury and for determination of the temporal stage of the repair phase at early time points after acute kidney injury. This will help in risk stratification of patients. In addition, these tests will facilitate the evaluation of therapeutic regimens, which depend on a precise temporal stage assessment in patients with acute kidney injury.

Surprisingly Chac1, Birc5 and/or Angptl7 are biomarkers which can be used in the early diagnosis of acute kidney injury, therefore guiding targeted intervention and monitoring of renal tubular cell injury progression. These biomarkers provide information on acute kidney injury at very early time points, thereby informing medical practitioners of the temporal phase of kidney injury in relation to phases which were previously both poorly categorised and difficult to obtain information about, thereby providing new opportunities for early intervention in kidney treatment. For the therapy of renal tubular cell injury it is very important to determine the stage and/or the time point of the injury. Until know it was only possible to estimate these parameters, especially in relation to the specific and early time points characterised by expression of the biomarkers according to the present invention. Due to these reasons the teaching of the present invention satisfies of a long-felt need in the field of kidney injury diagnosis.

Since it is important to diagnose kidney injuries as fast as possible, there is a requirement that diagnostic methods can be carried out accurately and quickly, in order to provide medical practitioners with reliable information obtained in as quickly a manner as possible. Therefore it is a great advantage that the method of the invention can be adapted for use in an automated system or semi-automated system. This embodiment not only realises saving of time, but also of material, work steps and costs.

It is preferred, that a sample is tested for all three biomarkers Chac1, Birc5 and Angptl7. This embodiment of the invention exhibits the advantage, that stage of renal tubular cell injury can be determined very exactly. This leads to great advantages in considering appropriate treatments for patients having had kidney injury. However, the biomarkers of the present invention can also be used individually in order to determine temporal phase of kidney injury and recovery. In light of the prior art, there are currently no known markers that exhibit the properties of the markers disclosed herein, namely that due to strong but precise expression in specific time windows, namely the early early and late early phases, the temporal phase and time point of the injury can be determined, thus enabling accurate and informed treatment options for medical practitioners. Because the unifying technical and functional features of the biomarkers encompassed by the present invention are both novel and inventive in light of what is currently available in the art, the claimed method and use of the biomarkers represent a single unified invention.

The method of the present invention is in a preferred embodiment characterized in that the method comprises one or more analytical techniques for analysis of the test sample selected from the group consisting of:
  DNA analysis, such as the analysis of DNA methylation via bisulfite cloning and sequencing of genomic DNA, direct bisulfite sequencing, bisulfite-specific polymerase chain reaction (PCR) sequencing, pyrosequencing, methylation-sensitive PCR, using preferably quantitative or real-time PCR, HPLC, mass spectrometry, microarray analysis, methylated DNA immunoprecipitation, methylated CpG amplification coupled to microarrays, or any other method for DNA analysis,
  RNA analysis, such as northern blot, in situ hybridization, techniques based on the use of reverse transcriptase, especially in combination with (PCR), such as quantitative PCR, quantitative real time (RT)-PCR, or any other method for RNA analysis
  Serological analysis, such as immunoassays, western-blotting, ELISA (Enzyme-Linked Immunosorbent Assay), RIA (Radioimmunoassay), Competitive EIA (Competitive Enzyme Immunoassay), DAS-ELISA (Double Antibody Sandwich-ELISA), immunocytochemical techniques, immunohistochemical techniques, techniques based on the use of biochips, techniques based on the use of protein microarrays that include specific antibodies, assays based on the precipitation of colloidal gold in formats, affinity chromatography techniques and ligand binding assays, or any other method of protein analysis, and/or
  combinations of the above, such as chromatin immunoprecipitation (ChIP), combined with PCR, such as RT-PCR or qRT-PCR, or any nucleotide-based array or sequencing approach, for examining chromatin environment and/or histone modifications (eg acetylation, methylation) surrounding biomarker genes of interest, therefore analyzing an activated or repressed state of biomarker-encoding genes.

DETAILED DESCRIPTION OF THE INVENTION

The present invention discloses phase-specific biomarkers of acute kidney injury. The biomarkers of the present invention allow determination of the time point of kidney injury due to their specific expression profiles. Until now, other biomarkers for kidney injury exhibit continued expression long after the injury, thereby providing no temporal phase-specific information on the injury that has occurred.

Surprisingly Chac1 was identified as a gene which is specifically induced in the early early phase after acute kidney injury, but returns to baseline levels within 30 to 70 hours, preferred 40 to 60 hours, especially preferred 48 hours after injury. So far, little has been disclosed regarding Chac1 and nothing has been published regarding Chac1 in matters of kidney injury and regeneration. Therefore it was very surprising that Chac1 was identified as a biomarker for the early early phase of acute kidney injury.

In addition Birc5 was identified as a gene which is induced selectively in the late early phase of kidney regeneration, 30 hours to 7 days, preferred 40 hours to 6 days, especially preferred 48 hours to 5 days after the event.

The biomarkers of the invention Chac1 and Angptl7 were identified as biomarkers for the early early phase after ischemia reperfusion injury and are highly and exclusively expressed 4 to 10 h, preferred 6 h post injury. Also preferred is the method as described herein, whereby both maximum expression of Chac1 and/or Angptl7 occurs during the early early phase of acute injury, preferred 4 to 10 hours, especially preferred 6 hours after ischemic renal tubular cell injury, and that maximum expression of Birc5 occurs during the late early stage, preferred 30 to 70 hours, more preferred 48 hours, after acute kidney injury.

The early early phase of acute kidney injury occurs shortly after kidney injury, preferably between 0 and 36 hours after injury, more preferably between 0 and 24 hours after injury and still more preferably between 0 and 12 hours after injury. The early early phase corresponds preferably to the hyperacute phase of acute kidney injury, and is preferably pathophysiologically characterized by tubular cell decay (apoptosis or necrosis) and an acute tubular stress response.

The late early phase of acute kidney injury occurs after the early early stage of acute kidney injury, preferably between 36 and 120 hours after injury, more preferably between 40 and 96 hours after injury, or preferably between 44 and 72 hours after injury. The late early phase corresponds preferably to the tubular proliferative phase (or regenerative phase) of an acute kidney injury and is preferably pathophysiologically characterized by tubular epithelial cell proliferation.

Elevated levels of Chac1 and/or Angptl7 indicate the early early phase of acute kidney injury. This phase corresponds to 0 to 36 hours post injury in the mouse model of ischemia-reperfusion injury, which is intended as an example for the analogous phase in humans. This phase may correspond to different time points in human postischemic kidney injury or in other types of kidney injury. Elevated levels of Birc5 indicate the late early phase of acute kidney injury. This phase corresponds to 36 to 120 hours post injury in the mouse model of ischemia-reperfusion injury, which is intended as an example for the analogous phase in humans. This phase may correspond to different time points in human postischemic kidney injury or in other types of kidney injury.

Because the early early and late early phases are in a preferred embodiment determined by the pathophysiological properties of the kidney, the time windows observed in the mouse models serve as relevant examples for the analogous time windows in humans, which can easily be controlled or ascertained by one skilled in the art in light of the disclosure provided with the present invention, and are therefore encompassed by the present invention.

In addition to the temporal phase determination due to increased expression levels of the biomarkers, the converse may be applied, so that low levels of Chac1 and/or Angptl7 exclude the early early phase of acute kidney injury, and that low levels of Birc5 exclude the late early phase of acute kidney injury.

The terms determination or measuring of "expression level" relates to the measurement or analysis of any indicator of biomarker expression, regarding preferably the measurement of biomarker presence. Expression level of a biomarker may include gene expression or activity, such as direct measurements of transcription, such as RNA production or RNA accumulation either intra- or extra-cellular, or indirect measurements of transcription, for example analysis of chromatin environment surrounding the gene coding for the biomarker, thereby indicating whether transcription of the biomarker gene is ongoing and to what extent. Chromatin modifications and their relationship to gene transcription are known in the art. Protein expression or accumulation is also encompassed within "expression level", either of intra- or extra-cellular protein. According to the central dogma of genetic information, as is understood by those skilled in the art, the flow of information from gene (DNA) to RNA to protein is linked, so that the biomarker expression level may relate to measurement of the level of any molecule related to the expression or production to any of the herein described biomarkers.

As used herein, the terms "subject" and "patient" are used interchangeably irrespective of whether the subject has or is currently undergoing any form of treatment. As used herein, the terms "subject" and "subjects" especially refer to a mammal including, a non-primate (for example, a cow, pig, camel, llama, horse, goat, rabbit, sheep, hamsters, guinea pig, feline, canine, rat, and murine), a non-human primate (for example, a monkey, such as a cynomolgous monkey, chimpanzee, etc) and a human. Preferably, the subject is a human.

The term "use as a biomarker" especially includes in this context in particular the following usages:
  diagnosis of the aforementioned diseases and pathological changes
  determination of the severity of the aforementioned diseases and pathological changes
  monitoring of the effects of interventions, such as pharmacotherapy, surgery, use of medicinal products and measures accompanying therapy, on the aforementioned diseases and pathological changes
  use as a surrogate marker, which replaces the determination of another parameter, which helps to assess the aforementioned diseases and pathological changes.

As used herein, the term "test sample" especially refers to a biological sample derived from tissue, kidney tissue, serum, plasma, blood (including, but not limited to, whole blood), lymph, urine or other bodily fluids of a subject. The test sample can be prepared using routine techniques known to those skilled in the art. Preferably, the test sample is urine, tissue or blood. A control sample in the meaning of the present invention can relate to a sample obtained from either a healthy (negative control) or diseased (positive control) individual or subject. Control samples may also relate to synthetic or artificially prepared samples comprising the biomarker molecules of the present invention for use as reference samples. Control samples and methods of their creation are known to those skilled in the art.

For the recitation of numeric ranges herein, each intervening number there between with the same degree of precision is explicitly contemplated. For example, for the range 6-9, for example, the numbers 7 and 8 are contemplated in addition to 6 and 9, and for the range 6.0-7.0, for example, the numbers 6.0, 6.1, 6.2, 6.3, 6.4, 6.5, 6.6, 6.7, 6.8, 6.9 and 7.0 are explicitly contemplated.

Antibodies:

As used herein, the terms "antibody" and "antibodies" especially refer to monoclonal antibodies, multispecific antibodies, human antibodies, humanized antibodies (fully or partially humanized), animal antibodies (in one aspect, a bird (for example, a duck or goose), in another aspect, a shark or whale, in yet another aspect, a mammal, including a non-primate (for example, a cow, pig, camel, llama, horse, goat, rabbit, sheep, hamsters, guinea pig, feline, canine, rat, murine, etc) and a non-human primate (for example, a monkey, such as a cynomologous monkey, a chimpanzee, etc), recombinant antibodies, chimeric antibodies, single-chain Fvs (scFv), single chain antibodies, single domain antibodies, Fab fragments, F(ab') 2 fragments, disulfide-linked Fv (sdFv), and anti-idiotypic (anti-Id) antibodies (including, for example, anti-Id antibodies to antibodies of the present invention), and functionally active epitope-binding fragments of any of the above. In particular, antibodies include immunoglobulin molecules and immunologically active fragments of immunoglobulin molecules, namely, molecules that contain an antigen binding site. Immunoglobulin molecules can be of any type (for example, IgG, IgE, IgM, IgD, IgA and IgY), class (for example, IgG1, IgG2, IgG3, IgG4, IgA1 and Ig.2) or subclass. For simplicity sake, an antibody against an analyte is frequently referred to as being either an "anti-analyte antibody", or merely an "analyte antibody" (e.g., a Chac1 antibody).

The antibodies employed in the immuno- or serological assays of the present invention can be made using a variety of different techniques known in the art. For example, polyclonal and monoclonal antibodies against wild-type Chac1-, Birc5- and/or Angptl7 can be raised by immunizing a suitable subject (such as, but not limited to, a rabbit, goat, murine or other mammal) with an immunogenic preparation which contains a suitable immunogen. The immunogen that can be used for the immunization can include cells. Alternatively, the immunogen can be the purified or isolated human wild-type Chac1, Birc5 and/or Angptl7 protein itself or a human Chac1, Birc5 and/or Angptl7 fragment thereof. For example, wild-type human Chac1, Birc5 and/or Angptl7 that has been isolated from a cell which produces the protein using affinity chromatography, immunoprecipitation or other techniques which are well known in the art, can be used as an immunogen. Alternatively, immunogen can be prepared using chemical synthesis using routine techniques known in the art (such as, but not limited to, a synthesizer).

The antibodies raised in the subject can then be screened to determine if the antibodies bind to wild-type Chac1, Birc5 and/or Angptl7 or fragments thereof. Such antibodies can be further screened using the methods known in the state of art. For example, these antibodies can be assayed to determine if they bind to Chac1, Birc5 and/or Angptl7 or fragments thereof.

The unit dose of immunogen (namely, the purified protein, tumor cell expressing the protein, or recombinantly expressed Chac1, Birc5 and/or Angptl7 protein) and the immunization regimen will depend upon the subject to be immunized, its immune status, and the body weight of the subject. To enhance an immune response in the subject, an immunogen can be administered with an adjuvant, such as Freund's complete or incomplete adjuvant. Immunization of a subject with an immunogen as described above induces a polyclonal antibody response. The antibody titer in the immunized subject can be monitored over time by standard techniques such as an ELISA using an immobilized antigen, namely, Chac1, Birc5 and/or Angptl7 or fragments thereof.

Immunoassays:

Immunoassays can be conducted using any format known in the art, such as, but not limited to, a sandwich format. Specifically, in one aspect of the present invention, at least two antibodies are employed to separate and quantify Chac1, Birc5 and/or Angptl7 or fragments thereof in a test sample. More specifically, the at least two antibodies bind to certain epitopes of Chac1, Birc5 and/or Angptl7 or fragments thereof forming an immune complex which is referred to as a "sandwich". Generally, in the immunoassays one or more antibodies can be used to capture the Chac1, Birc5 and/or Angptl7 or fragment thereof in the test sample (these antibodies are frequently referred to as a "capture" antibody or "capture" antibodies) and one or more antibodies can be used to bind a detectable (namely, quantifiable) label to the sandwich (these antibodies are frequently referred to as the "detection antibody", "detection antibodies", a "conjugate" or "conjugates").

The test sample being tested for Chac1, Birc5 and/or Angptl7 or fragment thereof can be contacted with at least one capture antibody (or antibodies) and at least one detection antibody (which is either a second detection antibody or a third detection antibody) either simultaneously or sequentially and in any order. For example, the test sample can be first contacted with at least one capture antibody and then (sequentially) with at least one detection antibody. Alternatively, the test sample can be first contacted with at least one detection antibody and then (sequentially) with at least one capture antibody. In yet another alternative, the test sample can be contacted simultaneously with a capture antibody and a detection antibody.

In the sandwich assay format, a test sample suspected of containing Chac1, Birc5 and/or Angptl7 or fragment thereof is first brought into contact with an at least one first capture antibody under conditions which allow the formation of a first antibody/Chac1, Birc5 and/or Angptl7 complex. If more than one capture antibody is used, a first multiple capture antibody/Chac1, Birc5 and/or Angptl7 complex is formed. In a sandwich assay, the antibodies, preferably, the at least one capture antibody, are used in molar excess amounts of the maximum amount of Chac1, Birc5 and/or Angptl7 or fragment thereof expected in the test sample. For example, from about 5 µg/mL to about 1 mg/mL of antibody per mL of buffer (e.g., microparticle coating buffer) can be used.

Optionally, prior to contacting the test sample with the at least one capture antibody (for example, the first capture antibody), the at least one capture antibody can be bound to a solid support which facilitates the separation the first antibody/Chac1, Birc5 and/or Angptl7 complex from the test sample. Any solid support known in the art can be used, including, but not limited to, solid supports made out of polymeric materials in the forms of wells, tubes or beads. The antibody (or antibodies) can be bound to the solid support by adsorption, by covalent bonding using a chemical coupling agent or by other means known in the art, provided that such binding does not interfere with the ability of the antibody to bind Chac1, Birc5 and/or Angptl7 or fragment thereof. Alternatively, the antibody (or antibodies) can be bound with microparticles that have previously coated with streptavidin or biotin. Alternatively, the antibody (or antibodies) can be bound using microparticles that have been previously coated with anti-species specific monoclonal antibodies. Moreover, if necessary, the solid support can be derivatized to allow reactivity with various functional groups on the antibody.

After the test sample being tested for and/or suspected of containing Chac1, Birc5 and/or Angptl7 or fragment thereof is brought into contact with the at least one capture antibody (for example, the first capture antibody), the mixture is incubated in order to allow for the formation of a first antibody (or multiple antibody)-Chac1, Birc5 and/or Angptl7 complex.

After formation of the (first or multiple) capture antibody/Chac1, Birc5 and/or Angptl7 complex, the complex is then contacted with at least one detection antibody (under conditions which allow for the formation of a (first or multiple) capture antibody/Chac1, Birc5 and/or Angptl7/second antibody detection complex). The at least one detection antibody can be the second, third, fourth, etc. antibodies used in the immunoassay. Preferably, at least one detection antibody contains a detectable label. The detectable label can be bound to the at least one detection antibody (e.g., the second detection antibody) prior to, simultaneously with or after the formation of the capture antibody/Chac1, Birc5 and/or Angptl7/(second or multiple) detection antibody complex. Any detectable label known in the art can be used. For example, the detectable label can be a radioactive label, such as, $^{3}H$, $^{125}I$, $^{35}S$, $^{14}C$, $^{32}P$, $^{33}P$, an enzymatic label, such as horseradish peroxidase, alkaline phosphatase, glucose 6-phosphate dehydrogenase, etc., a chemiluminescent label, such as, acridinium esters, luminal, isoluminol, thioesters, sulfonamides, phenanthridinium esters, etc. a fluorescence label, such as, fluorescein, rhodamine, phycobiliproteins, R-phycoerythrin, quantum dots, a thermometric label or an immuno-polymerase chain reaction label.

The detectable label can be bound to the antibodies either directly or through a coupling agent. Various coupling agents that can be used are known in the art. Methods for binding a detectable label to an antibody are known in the art.

The capture antibody/human Chac1, Birc5 and/or Angptl7/detection antibody complex can be, but does not have to be, separated from the remainder of the test sample prior to quantification of the label. For example, if the at least one capture antibody is bound to a solid support, such as a well or a bead, separation can be accomplished by removing the fluid of the test sample from contact with the solid support.

After formation of the labeled capture antibody/Chac1, Birc5 and/or Angptl7/detection antibody complex, the amount of label in the complex is quantified using techniques known in the art. For example, if an enzymatic label is used, the labeled complex is reacted with a substrate for the label that gives a quantifiable reaction such as the development of colour. If the label is a radioactive label, the label is quantified using a scintillation counter. If the label is a fluorescent label, the label is quantified by stimulating the label with a light of one colour and detecting another colour that is emitted by the label in response to the stimulation. If the label is a chemiluminescent label, the label is quantified detecting the light emitted either visually or by using luminometers, x-ray film, high speed photographic film, etc. Once the amount of the label in the complex has been quantified, the concentration of Chac1, Birc5 and/or Angptl7 or fragment thereof in the test sample is determined by use of a standard curve that has been generated using serial dilutions of Chac1, Birc5 and/or Angptl7 or fragment thereof of known concentration. Other than using serial dilutions of Chac1, Birc5 and/or Angptl7 or fragment thereof, the standard curve can be generated gravimetrically, by mass spectroscopy and by other techniques known in the art.

Disorders and Injury Definitions:

An "acute kidney injury" or "acute renal tubular cell injury" includes acute ischemic renal injury (IRI), acute nephrotoxic renal injury (NRI) in addition to renal injury (RI) of other origins. Although the examples provided herein deal primarily with ischemic renal injury, the findings are also relevant for nephrotoxic renal injury and renal injury of other origins due to the similarities in kidney response in all types of injury. IRI includes but is not limited to ischemic injury, chronic ischemic injury, acute renal failure and acute tubular necrosis. Further renal injuries of other origins include but are not limited to acute glomerulonephritis and acute tubulo-interstitial nephropathy. NRI toxicity includes but is not limited to, sepsis (infection), shock, trauma, kidney stones, kidney infection, drug toxicity, poisons or toxins, or after injection with a radiocontrast dye. Kidney injuries of the invention relate to all disease mentioned in N17-N19 of the WHO classification.

As used herein the expression "renal tubular cell injury" especially means a renal or kidney failure or dysfunction, either sudden (acute) or slowly declining over time (chronic), that can be triggered by a number of disease or disorder processes. Both acute and chronic forms of renal tubular cell injury can result in a life-threatening metabolic derangement.

The phrases "chronic renal tubular cell injury", "progressive renal disease", "chronic renal disease (CRD)", "chronic kidney disease (CKD)" as used interchangeably herein, especially include any kidney condition or dysfunction that occurs over a period of time, as opposed to a sudden event, to cause a gradual decrease of renal tubular cell function or worsening of renal tubular cell injury. One endpoint on the continuum of chronic renal disease is "chronic renal failure (CRF)". For example, chronic kidney disease or chronic renal injury as used interchangeably herein, includes, but is not limited to, conditions or dysfunctions caused by chronic infections, chronic inflammation, glomerulonephritides, vascular diseases, interstitial nephritis, drugs, toxins, trauma, renal stones, long standing hypertension, diabetes, congestive heart failure, nephropathy from sickle cell anemia and other blood dyscrasias, nephropathy related to hepatitis, HIV, parvovirus and BK virus (a human polyomavirus), cystic kidney diseases, congenital malformations, obstruction, malignancy, kidney disease of indeterminate causes, lupus nephritis, membranous glomerulonephritis, membranoproliferative glomerulonephritis, focal glomerular sclerosis, minimal change disease, cryoglobulinemia, Anti-Neutrophil Cytoplasmic Antibody (ANCA)-positive vasculitis, ANCA-negative vasculitis, amyloidosis, multiple myeloma, light chain deposition disease, complications of kidney transplant, chronic rejection of a kidney transplant, chronic allograft nephropathy, and the chronic effects of immunosuppressives. Preferably, chronic renal disease or chronic renal injury refers to chronic renal failure or chronic glomerulonephritis.

One example of acute kidney injury relates to post-operative kidney failure, a disorder that is exhibited in patients after surgical operation. Some operations are more inclined to be followed by acute kidney injury, such as in children who have undergone Cardiopulmonary bypass surgery (Krawczeski, et al, 2001, Journal of Pediatircs). The diagnosis of kidney injury in such cases is of utmost important, so that appropriate measures can be taken regarding therapeutic treatment.

Kits:

The present invention also encompasses kits for detecting the presence of Chac1, Birc5 and/or Angptl7 antigen in a test sample in improved assays. Such kits can comprise one or more of the immunodiagnostic reagents (e.g., antibodies or primers). More specifically, if the kit is a kit for performing an immunoassay, the kit optionally can contain (1) at least one capture antibody that specifically binds to Chac1, Birc5 and/or Angptl7; (2) at least one conjugate; and (3) one or more instructions for performing the immunoassay. The immunodiagnostic reagents of the present invention can be included in such a test kit as a capture antibody, as a detection antibody or both as a capture antibody and a detection antibody. Optionally, the kit can also contain at least one calibrator or control. Any calibrator or control can be included in the kit.

The kits can optionally include other reagents required to conduct a diagnostic assay or facilitate quality control evaluations, such as buffers, salts, enzymes, enzyme co-factors, substrates, detection reagents, and the like. Other components, such as buffers and solutions for the isolation and/or treatment of a test sample, may also be included in the kit. The kit may additionally include one or more other controls.

The various components of the kit optionally are provided in suitable containers. As indicated above, one or more of the containers may be a microtiter plate. The kit further can include containers for holding or storing a sample (e.g., a container or cartridge for a blood or urine sample). Where appropriate, the kit may also optionally contain reaction vessels, mixing vessels and other components that facilitate the preparation of reagents or the test sample. The kit may also include one or more instruments for assisting with obtaining a test sample, such as a syringe, pipette, forceps, measured spoon, or the like.

Sequences:

In a preferred embodiment the sequences as provided herein, in addition to sequences sharing 80%, 85%, 90%, 95% or more sequence identity to the sequences listed herein, are intended to fall within the scope of the invention. In another preferred embodiment, analysis of the DNA, RNA or corresponding protein sequence (for example protein translated from RNA arising from the relevant nucleic acid sequence) as described herein, or a part or fragment thereof, may be analysed in the method of the present invention.

Complementary sequences and/or degenerated sequences (degenerated according to the genetic code; sequences that therefore encode the same or similar amino acid sequence) also fall within the scope of the invention. The corresponding RNA sequences, which arise via transcription of the DNA sequences provided herein, are also encompassed in the present invention. RNA sequences that correspond to parts or fragments of the DNA sequences are also encompassed in the invention, especially spliced RNA sequences comprising exons after splice-mediated removal of introns. In light of the DNA sequences provided, the relevant corresponding RNA sequences are known to one skilled in the art and therefore encompassed herein.

For example, primer oligonucleotides may be produced by selecting sequences of, or sequences complementary to, the provided sequences or fragments thereof, in the design of PCR-based approaches for detecting and quantifying mRNA in test samples, or DNA sequences in the case of ChIP-based approaches. Such genomic analytical approaches are known to one skilled in the art and therefore encompassed herein.

The following sequences are encompassed within the scope of the invention.

TABLE 1

Sequences of the Invention

| Gene/Biomarker | Organism | SEQ ID NO. | DNA/protein |
|---|---|---|---|
| Chac1 | Human | SEQ ID NO. 1 | DNA |
| Chac1 | Human | SEQ ID NO. 2 | Protein |
| Chac1 | Mouse | SEQ ID NO. 3 | DNA |
| Chac1 | Mouse | SEQ ID NO. 4 | Protein |
| Chac1 | Rat | SEQ ID NO. 5 | DNA |
| Chac1 | Rat | SEQ ID NO. 6 | Protein |
| Birc5 | Human | SEQ ID NO. 7 | DNA |
| Birc5 | Human | SEQ ID NO. 8 | Protein |
| Birc5 | Mouse | SEQ ID NO. 9 | DNA |
| Birc5 | Mouse | SEQ ID NO. 10 | Protein |
| Birc5 | Rat | SEQ ID NO. 11 | DNA |
| Birc5 | Rat | SEQ ID NO. 12 | Protein |
| Angptl7 | Human | SEQ ID NO. 13 | DNA |
| Angptl7 | Human | SEQ ID NO. 14 | Protein |
| Angptl7 | Mouse | SEQ ID NO. 15 | DNA |
| Angptl7 | Mouse | SEQ ID NO. 16 | Protein |
| Angptl7 | Rat | SEQ ID NO. 17 | DNA |
| Angptl7 | Rat | SEQ ID NO. 18 | Protein |

FIGURES

The invention is further described by the figures. These are not intended to limit the scope of the invention.

DETAILED DESCRIPTION OF THE FIGURES

Figure 1:
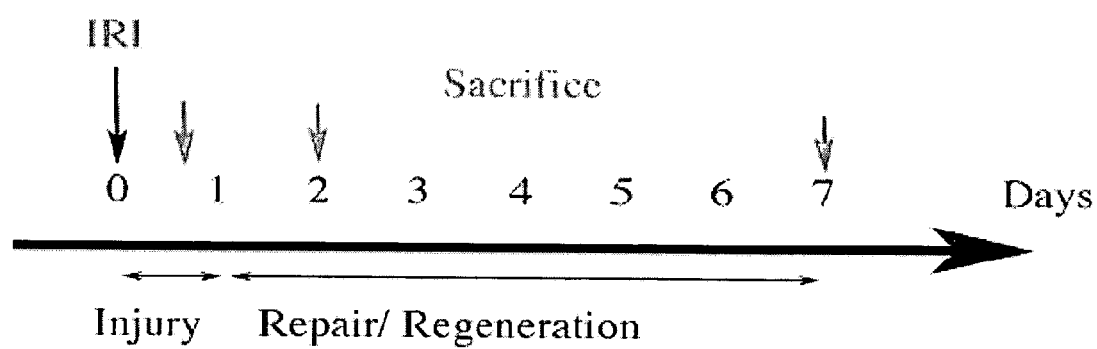
FIG. 1: Experimental Design

FIG. 1: Experimental Design. Ischemia reperfusion injury was performed at 10-12 weeks old C57BI/6 male mice. 6 h, 48 h and 7 d post injury kidneys, blood and urine was collected for stage-specific analysis of renal injury and regeneration.

Figure 2:
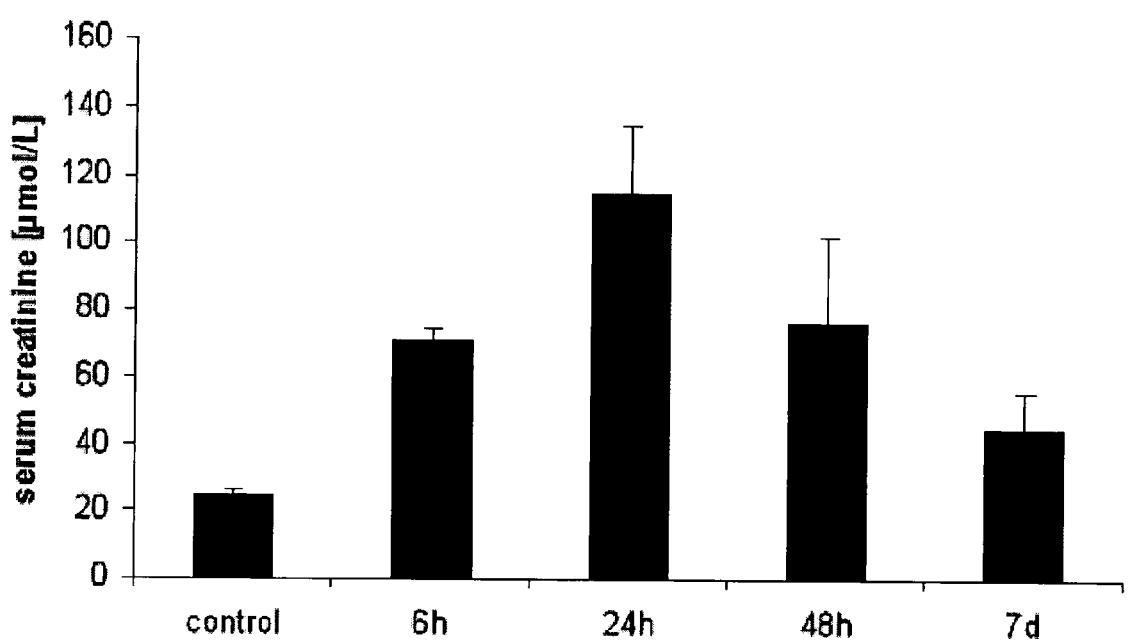
FIG. 2: Characterization of ischemia reperfusion injury followed by repair.
Figure 3:
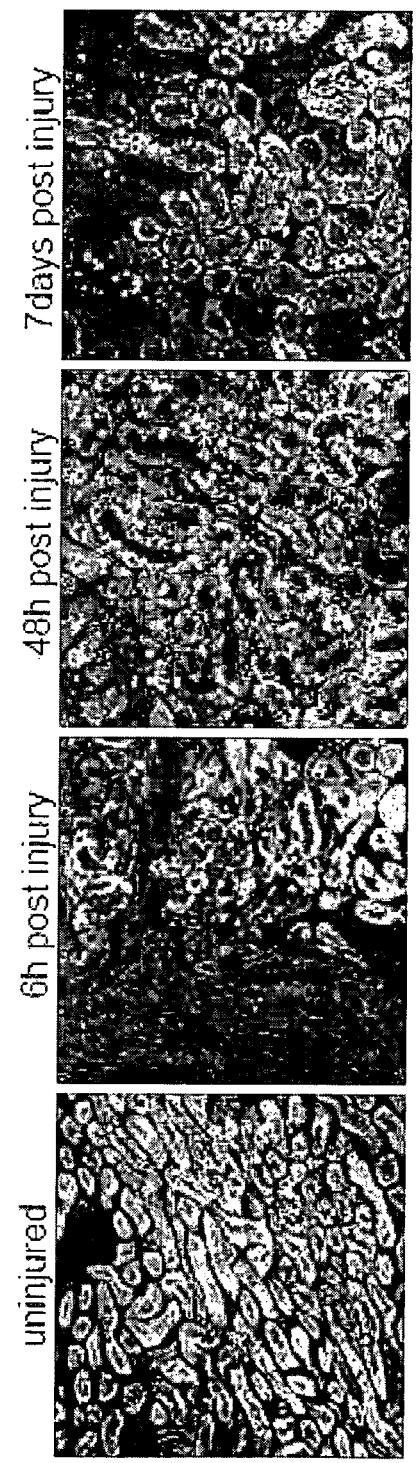
FIG. 3: Representative photomicrograph of adult C57BI/6 mouse kidneys labelled with antibodies against Ki67

FIG. 2: Characterization of ischemia reperfusion injury followed by repair. Serum creatinine levels in C57BI/6 mice in days following kidney ischemia reperfusion injury (n≥6; mean±SEM). uninjured 6 h post injury 48 h post injury 7 days post injury FIG. 3: Representative photomicrograph of adult C57BI/6 mouse kidneys labelled with antibodies against Ki67 (light spots). Tubular autofluorescence of the kidney is shown in grey. Form left to right (A) sham, (B) 6 h, (C) 48 h and (D) 7 days kidneys post injury are depicted. Most epithelial proliferation occurs early after injury (48 h). Ki67-positive tubular nuclei were identified in outer medulla of kidney sections at baseline and at 2 and 7 days after kidney injury.

Figure 4:
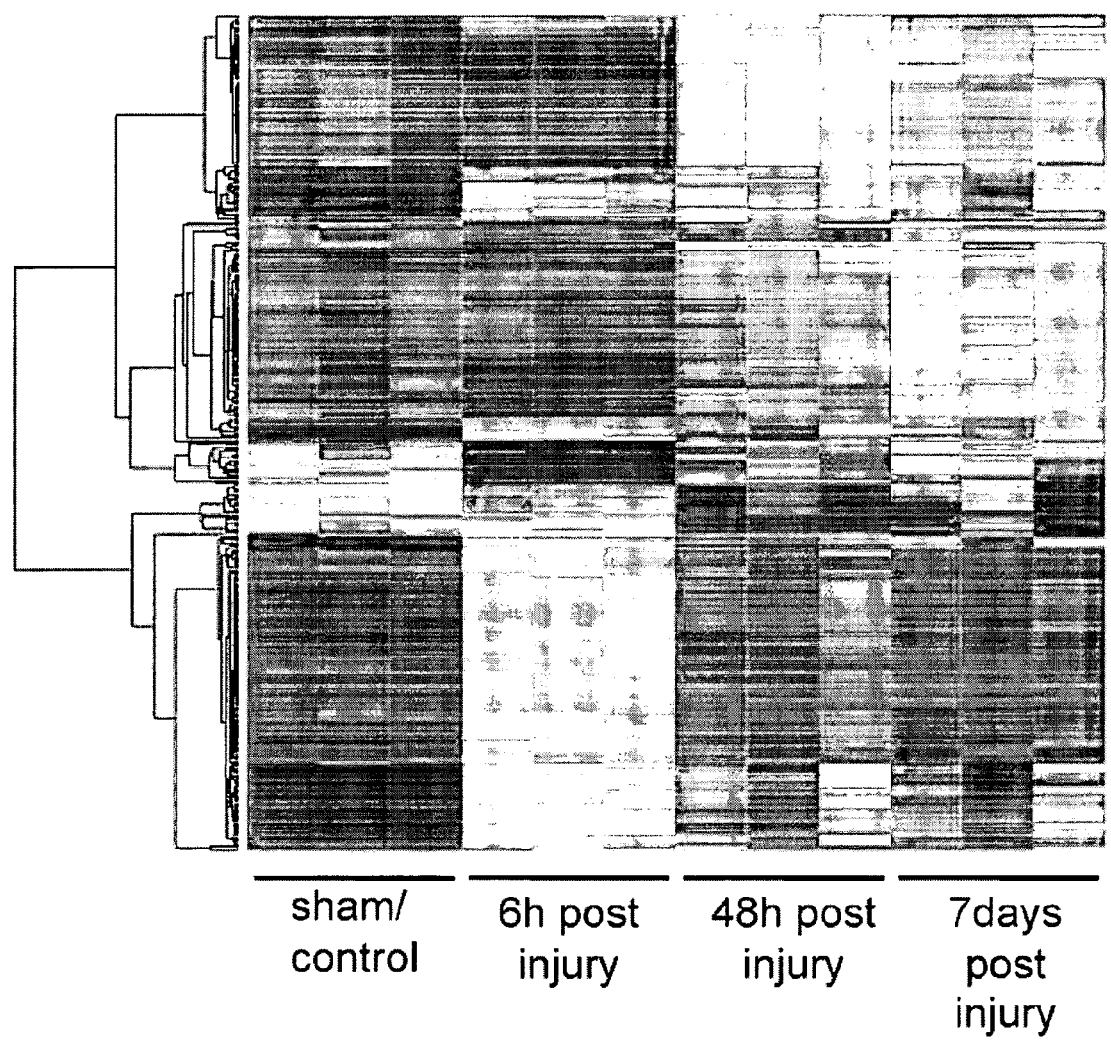
FIG. 4: Heatmap analysis of microarray data showing hierarchical clustering of post ischemic stage-specific expressed genes.

FIG. 4: Heatmap analysis of microarray data showing hierarchical clustering of post ischemic stage-specific expressed genes. Gene expression of sham/contralateral (1-3), 6 h (4-6), 48 h (7-9) and 7 days kidneys post injury are depicted from left to right (each n=3). Light or dark colours indicate differentially up- or downregulated genes, respectively.

Figure 5:
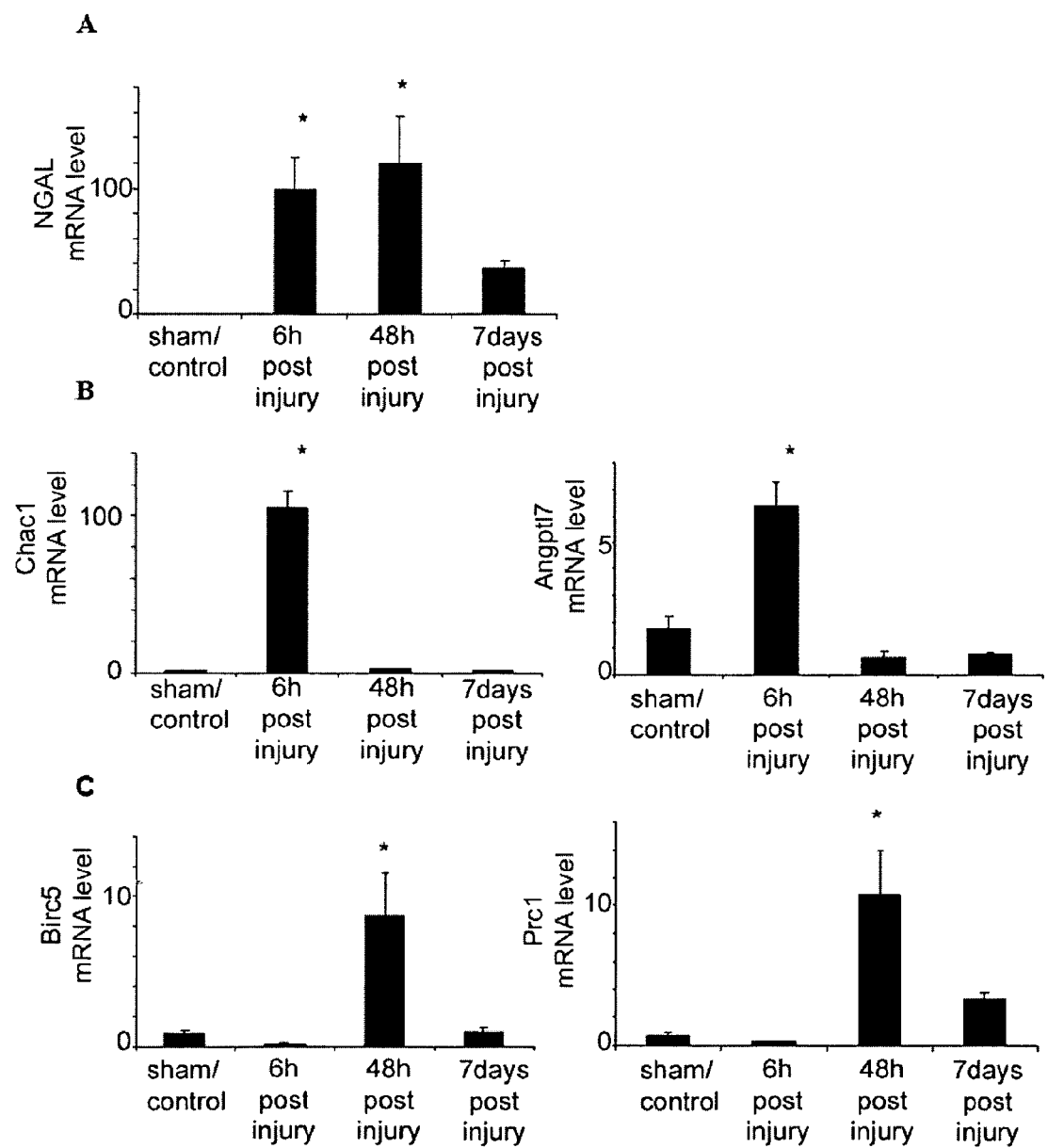
FIG. 5: Ischemia reperfusion injury in C57BI/6 mice results in stage specific gene activation in the renal regeneration phase.

FIG. 5: Ischemia reperfusion injury in C57BI/6 mice results in stage specific gene activation in the renal regeneration phase. Real-time RT-PCR for mRNA of whole C57BI/6 mice kidneys collected 6 hours, 48 hours and 7 days after ischemia reperfusion injury. Each bar represents at least 6 different biological replicates. *$p<0.05$ vs. control (contralateral and sham kidneys). Relative mRNA expression of (A) NGAL, (B) Chac1, Angptl7 and (C) Birc5 and Prc1. ANOVA followed by the posthoc Tukey test was performed for statistical analysis (n≥0.6). Axin2+/LacZ sham Axin2+/LacZ 6 h post injury.

Figure 6:
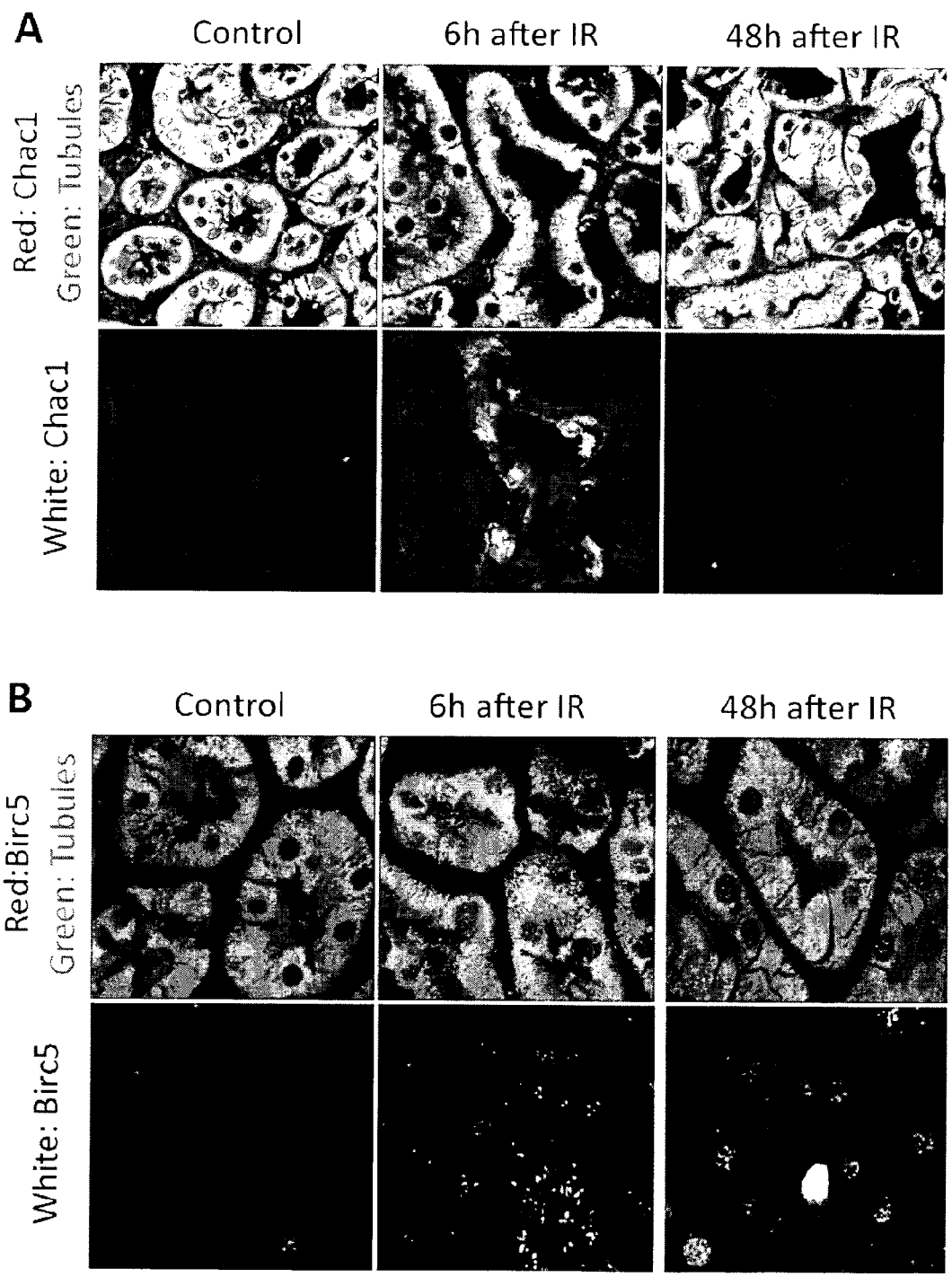
FIG. 6: Expression of Chac1 (A) and Birc5 (B) proteins in renal tubules following ischemia-reperfusion injury (IR) in mice as detected by immunofluorescence staining using antibodies specific for Chac1 or Birc5.

FIG. 6: Expression of Chac1 (A) and Birc5 (B) proteins in renal tubulkes following ischemia-reperfusion injury (IR) in mice as detected by immunofluorescence staining using antibodies specific for Chac1 or Birc5. "Green" staining in upper panels delineates renal tubular epithelial cells (marked by autofluorescence), whereby the structure of the tubules can be clearly observed. Chac1 protein is induced in tubular epithelial cells 6 h after injury, while markedly lower levels are observed in control kidneys (no IR injury) or kidneys 48 h after injury. Chac1 is a marker for the early early (hyperacute) phase of postischemic injury. Birc5 protein is induced in tubular epithelial cells 48 h after injury, while markedly lower levels are observed in control kidneys (no IR injury) or kidneys 6 h after injury. Bric5 is a marker for the late early (tubular proliferative) phase of postischemic injury.

EXAMPLES

The invention is further described by the following examples. These are not intended to limit the scope of the invention. The experimental examples relate, amongst others, to various in vivo experiments carried out in mouse models using induction of AKI via ischemia reperfusion injury. The mice models represent a mammal model, used to demonstrate the invention by way of example. Other mammals, preferably humans, can also be diagnosed using the subject matter of the present invention.

Methods Used in the Examples:

Animal Models

Induction of AKI via ischemia reperfusion injury: Male C57BI/6 mice (10-12 weeks old) were anesthetized with 2% isofluran. Nephrectomie of the right kidney was performed and a surgical clamp was placed across the left renal artery and vein. Kidneys were confirmed to become dusty. After 20 minutes clamps were removed and the return of perfusion to kidneys was confirmed before wound closure. The mice were sacrificed at 6 h, 48 h and 7 days post injury and the kidneys, blood and urine were collected for further analysis. Serum creatinine was measured with the iSTAT blood analyzer (Abbott). The left kidneys were quickly removed and processed for histologic evaluation and RNA extraction.

Sham operations without clamping of the renal arteries and contralateral kidneys served as normal controls.

Tissue Preparation and Immunostaining

Mouse kidneys were removed, decapsulated and cut into 2-3 mm thick pieces. For histological analysis, adult kidney slices were fixed for 60 min in 4% formaldehyde in PBS transferred in PBS containing 50 mM NH4Cl for 30 min, soaked overnight in PBS with 30% sucrose. Samples were embedded in Tissue-Tek O.C.T. Compound (Sakura Finetek Germany GmbH, Staufen, Germany) and were cut into 16 μm transverse sections and used for immunofluorescence staining. Slides were rinsed for 15 min in PBS. Sections were blocked with TNB for at least 1 h at RT and incubated overnight at 4° C. with Ki67 (1:200) in TNB. Bound antibodies were detected using Cy5 conjugated secondary antibodies (Jackson ImmunoResearch Europe Ltd., Newmarket, UK). Confocal fluorescent microscopy was performed on an inverted TCS SP5 Tandem confocal microscope.

RNA Isolation and cDNA Synthesis

Total kidney RNA expression was determined using RNA isolated with RNeasy Mini Kit (Qiagen, Hilden, Germany) according to manufacturer's instructions including treatment with RNase-Free DNase I (Qiagen, Hilden, Germany). First-strand cDNA synthesis was carried out with the RevertAid™ First Strand cDNA Synthesis Kit (Fermentas GmbH, St. Leon-Rot, Germany) according to the manufacturers' protocols.

Microarrays

The Illumina platform MouseWG-6 v2.0 Expression BeadChip Kit was used that assays more than 45,000 transcripts. The Kit was used according to the manufacturers' protocol.

Real-Time PCR

Real time PCR was performed using MESA GREEN qPCR MasterMix Plus for SYBR® Assay Rox (Eurogentec GmbH, Köln, Germany). Relative levels of mRNA expression were normalized for beta-actin mRNA expression and calculated according to the ΔΔCT method. For statistical analysis we used ANOVA followed by the posthoc Tukey test.

Example 1

Ischemia Reperfusion Experiments in Mouse Models

Ischemia reperfusion experiments were performed in (n=3 for the microarrays; n=3-7 for the validation of the microarrays) male C57Bl/6 mice. FIG. 1 shows the experimental design. Ischemia reperfusion injury was performed at 10-12 weeks old C57Bl/6 male mice. 6 h, 48 h and 7 d post injury kidneys, blood and urine was collected for stage-specific analysis of renal injury and regeneration.

The serum creatinine and NGAL as common biomarkers of acute kidney injury were determined to define the degree of injury and to monitor the regeneration process. Creatinine levels (FIG. 2) in control mice are 24.3+/−2.7 μmol/L. Post ischemia reperfusion injury creatinine levels rise from 70.5+/−3.7 μmol/L (6 h) to a maximum of 114.3+/−20.2 μmol/L after 24 hours. 48 hours post injury serum creatinine declined to 76.6+/−24.8 μmol/L and after seven days the levels are close to the physiological value (45+/−10.7 μmol/L). We isolated RNA from mouse kidneys and performed real time RT-PCR for NGAL as additional injury marker (FIG. 5A) and obtained results that correlate with serum creatinine. Relative to the control (sham kidneys), NGAL increased significantly after 6 h (99.8-fold +/−29.1 increase) and 48 hours (119.6-fold +1-37.6 increase) and decreased in the next days with an 36.3+/−5.8 fold-increase after 7 days (still representing substantially increased levels).

Next we focused on the characterization of the proliferative response at the three different time points. The results (FIG. 3) showed, that the majority of tubular epithelial cells are positive for the proliferation marker Ki67 after 48 hours whereas nearly no interstitial cells proliferate. 6 h post injury very few cells proliferate comparable to the control and 7 days after ischemia reperfusion injury still some tubular cells proliferate. Following we performed microarray analysis with the four groups (sham/contralateral, 6 h, 48 h and 7 days post injury; n=3). FIG. 4 depicts a heatmap analysis of microarray data showing hierarchical clustering of post ischemic stage-specific expressed genes. Each time window (sham, 6 h, 48 h and 7 d) demonstrates genes that are exclusively expressed at this stage and absent in all other phases of kidney injury and regeneration. As predicted from our immunostaining, the microarray analysis of these samples showed an upregulation of proliferation-associated genes solely after 48 hours. There are several genes representing G2/M transition (Birc5, Cdca3, Cdc20, Ccnb1) and M/G1 transition (Pbk, Prc1, Cdkn3). Expression of this signature was specific for the tubular proliferative phase (48 hours after injury) and absent in early postischemic kidneys (6 hours after injury) and in the reconstitution phase (7 days after injury). The proliferative genes were even down-regulated 6 h post injury indicating an antiproliferative and pro-apoptotic gene signature for this early time point. The expression of these genes were validated using real-time RT-PCR and included additional injured mice (FIG. 5C). All proliferative genes mentioned above have been validated via real time RT-PCR (data not shown). We proved a significant increase of Birc5 and Prc1 after 48 hours relative to sham and contralateral mice (FIG. 5C).

Chac1 and/or Angptl7 are a selection of two genes highly and exclusively up-regulated 6 hours post injury (FIG. 5B). Chac1 is a proapoptotic component of the unfolded protein response, downstream of the ATF4-ATF3-CHOP cascade and significantly up-regulated (105+/−10.4 fold) in real time RT-PCR after 6 h.

To identify stage-specific genes in the repair phase of acute kidney injury (AKI) as biomarkers for targeted therapy we analyzed gene expression signatures at three different time points (6 h, 48 h and 7 d) during the recovery phase after ischemia reperfusion injury in mice performing microarray analysis. In the early phase 6 h post injury an antiproliferative and proapoptotic gene signature was found. We observed a co-activation of genes of the ATF4-ATF3-CHOP-CHAC1 pathway which respond to endoplasmatic reticular stress and of the WNT/beta-catenin pathway. Two potential biomarkers for the first acute phase after renal injury (Chac1 and Angptl7) were identified that are highly and exclusively expressed 6 h post injury. Chac1 is a proapoptotic component of unfolded protein response downstream of ATF4-ATF3-CHOP signalling and Angptl7 is a potential target gene of WNT/beta-catenin signalling. 48 hours post injury a proliferative gene signature was observed which correlates with a former study that demonstrates highest proliferative response 48 h after ischemia reperfusion injury via immunofluorescence imaging. We identified proliferation associated genes highly and specifically expressed at this time-point and selected potential biomarkers for this post ischemic phase (Birc5 and Prc1) for further analysis.

Further experiments were carried out using tissue samples obtained from injured or un-injured kidneys and immunofluorescence staining. As is clearly demonstrated in FIG. 6 antibodies specific for Chac1 and Birc5 were used to detect evidence of biomarker expression at specific time points.

Example 2

Diagnostic Examples in Patients

The following diagnostic examples in patients are provided:

A 65-yo patient acutely hospitalized for pneumonia is evaluated for biomarker-positive acute kidney injury. The creatinine is 1.3 mg/dl or a similar value, the urinary NGAL level is 205 ng/ml or a similar value, suggesting intrinsic acute kidney injury of unknown duration. Other biomarkers (e.g. plasma NGAL, urinary Kim-1, L-FABP, interleukin-18, and/or cystatin C) may also be used to diagnose intrinsic acute kidney injury. Spot measurements of all of these markers revealing potentially positive signals do not reveal the exact phase of acute kidney injury, since they are elevated for sustained periods after acute kidney injury. A kidney biopsy is performed and Chac1, Angptl7 and/or Birc5 levels are measured in this tissue specimen.

Alternatively, urine or blood samples are obtained and Chac1, Angptl7 and/or Birc5 levels are measured in these biofluids.

Several scenarios may arise:

Chac1 and/or Angptl7 levels are elevated. Birc5 levels are within the normal range. These results indicate the early early phase of acute kidney injury. Creatinine and NGAL levels will likely increase further. The patient is transferred to an intensive care unit and kidney-protective therapy is instituted.

Chac1 and/or Angptl7 levels are within normal limits. Birc5 levels are elevated. This indicates that intrinsic acute kidney injury occurred several days ago, that the acute kidney injury is in the late early phase and the kidney is now undergoing a regenerative response. Creatinine and NGAL levels are still increased and likely to normalize to baseline values in the future. The patient is transferred to a regular ward and nephrotoxic substances are avoided.

Chac1 and/or Angptl7 levels are within normal limits. Birc5 levels are within normal limits. This indicates that acute kidney injury occurred many days ago and that the early early and late early phases of the kidney injury are now past. Creatinine level is likely not going to drop further. NGAL levels are still increased and may decrease further eventually. The patient has a favourable prognosis and is transferred to a regular ward. Nephrotoxic medication may be applied if necessary.

A 55-yo patient with known remitting autoimmune disease (e.g. Wegener's granulomatosis) is hospitalized for progressive renal failure of unknown duration. His creatinine is increased to 5.5 mg/dl or a similar value from a previous creatinine of 1.8 mg/dl or similar 6 months ago, the urinary NGAL level is 550 ng/ml or a similar value, suggesting ongoing intrinsic acute kidney injury. A kidney biopsy is performed and Chac1, Angptl7 and/or Birc5 levels are measured in this tissue specimen. Alternatively, urine or blood samples are obtained and Chac1, Angptl7 and/or Birc5 levels are measured in these biofluids. Urinalysis and histology suggest necrotizing glomerulonephritis of unknown duration with evidence of chronic changes. Other parameters of disease activity are non-revealing.

Several scenarios may arise:

Chac1 and/or Angptl7 levels are elevated. Birc5 levels are within the normal range. These results indicate an ongoing early early phase of intrinsic acute kidney injury. Creatinine and NGAL levels will likely increase further. The patient requires immediate therapy. The patient is closely monitored, high dose corticosteroids and cyclophosphamide pulse therapy are initiated.

Chac1 and/or Angptl7 levels are within normal limits. Birc5 levels are elevated. This indicates that intrinsic acute kidney injury occurred several days ago, the injury has progressed to the late early phase and the kidney is now undergoing a regenerative response. Creatinine and NGAL levels are still increased and are likely to normalize to baseline values eventually. A watch-and wait strategy is employed.

Chac1 and/or Angptl7 levels are within normal limits. Birc5 levels are within normal limits. This indicates that acute kidney injury occurred many days ago and that the early early and late early phase responses of the kidney are now past. Creatinine level is likely not going to drop further. NGAL levels are still increased and may decrease further eventually. The patient is transferred to a regular ward, no immunosuppressive therapy is initiated, chronic hemodialysis is initiated.

Further examples relate to the following scenarios:

A patient with biomarker-positive acute kidney injury is evaluated for inclusion into a study to test a novel therapeutic strategy for the treatment of acute kidney injury. Based on data in animal models, the novel strategy is only promising, if applied in the early early phase of acute kidney injury. Therefore, a kidney biopsy is performed and Chac1, Angptl7 and/or Birc5 levels are measured in this tissue specimen. Alternatively, urine or blood samples are obtained and Chac1, Angptl7 and/or Birc5 levels are measured in these biofluids. Only patients with elevated levels of Chac1 and/or Angptl7 are included into the study, since this reflects the earliest phase of acute kidney injury. Alternatively, only patients who display low levels of Birc5 are included into the study, since this excludes progression to the late early phase.

A patient with biomarker-positive acute kidney injury is evaluated for inclusion into a study to test a novel therapeutic strategy for the treatment of acute kidney injury. Based on data in animal models, the novel strategy is only promising, if applied during the late early phase of acute kidney injury. Therefore, a kidney biopsy is performed and Chac1, Angptl7 and/or Birc5 levels are measured in this tissue specimen. Alternatively, urine or blood samples are obtained and Chac1, Angptl7 and/or Birc5 levels are measured in these biofluids. Only patients with elevated levels of Birc5 are included into the study, since this reflects the late early phase of acute kidney injury. Alternatively, only patients who display low levels of Chac1 and/or Angptl7 are included into the study, since this excludes the presence of early early kidney injury.

An experimental study is carried out in patients or mice to test the effect of a genetic defect or alteration on the progression from the early early phase of acute kidney injury to the late early phase of acute kidney injury. As surrogate markers, Chac1 and/or Angpt7 and/or Birc5 are measured in kidney extracts and/or serum and/urine. Alternatively, an experimental study is carried out in patients or mice to test the effect of a therapeutic intervention on the progression from the early early phase of acute kidney injury to the late early phase of acute kidney injury. As surrogate markers, Chac1 and/or Angpt7 and/or Birc5 are measured in kidney extracts and/or serum and/urine.

The invention claimed is:

1. A method for determining a time of an acute kidney injury, comprising
   a. obtaining a test sample from a subject;
   b. determining, in said test sample, whether biomarkers Chac1 and/or Angptl7 are expressed above baseline levels and/or whether biomarker Birc5 is expressed above a baseline level, and
   c. determining, based on results obtained in b, the time when said acute kidney injury in said subject occurred, wherein the acute kidney injury occurred (i) between 0 and 36 hours before obtaining said test sample in a., when biomarkers Chac1 and/or Angptl7 are expressed above the baseline levels and/or (ii) between 0 and 120 hours before obtaining said test sample in a., when the biomarker Birc5 is expressed above the baseline level, wherein subsequent to the determining in c., renal injuries are treated or wherein when elevated levels of Chac1 and/or Angptl7 are detected, kidney-protective therapy is instituted.

2. The method according to claim 1, wherein severity of the acute kidney injury is determined.

3. The method according to claim 1, wherein the test sample is a urine, tissue or blood sample.

4. The method according to claim 1, wherein DNA, RNA and/or protein is/are analyzed in the test sample.

5. The method according to claim 1, wherein the method is adapted for use in an automated system and/or semi-automated system.

6. The method according to claim 1, wherein said acute kidney injury is an injury selected from the group consisting of a renal tubular cell injury, ischemic renal injury, a nephrotoxic injury, and any other injury that affects the tubular cells of the kidney.

7. The method according to claim 6, wherein one or more further biomarkers are analyzed before and/or in combination with analysis of expression levels of Chac1, Birc5 and/or Angptl7.

8. The method according to claim 7, wherein at least one of the biomarkers is expressed above the baseline level.

9. The method according to claim 7, wherein the one or more further biomarkers that are analyzed before and/or in combination with analysis of the expression level of Chac1, Birc5 and/or Angptl7 are—creatinine, neutrophil gelatinase-associated lipocalin (NGAL), interleukin 18 (IL-18), kidney injury molecule 1 (Kim-1) and/or Liver fatty acid binding protein (LFABP).

10. The method according to claim 1, wherein Chac1, Birc5 and/or Angptl7 is used for detecting the severity of acute kidney injury and/or as a therapy-accompanying or follow-up control biomarker.

11. The method according to claim 1, wherein an expression level is determined via an antibody which binds to Chac1, Birc5 or Angptl7.

12. The method according to claim 1, wherein said renal injuries are treated.

13. The method according to claim 1, wherein said kidney-protective therapy is instituted.

14. A method comprising:
   a. determining Chac1, Birc5 and/or Angptl7 expression level in a test sample obtained from a subject,
   b. comparing the Chac1, Birc5 and/or Angptl7 expression determined in said test sample with the expression level of Chac1, Birc5 and/or Angptl7 in a control sample, and
   c. timing the acute kidney injury based on the comparison in step b), wherein elevated levels of Chac1 and/or Angptl7 expression in said test sample in comparison to the control sample correspond to an acute kidney injury having occurred between 0 and 36 hours before obtaining said test sample, and/or elevated levels of Birc5 expression in said test sample in comparison to the control sample correspond to the acute kidney injury having occurred between 36 and 120 hours before obtaining said test sample, and
   d. detecting the timing of the acute kidney injury in the subject based on results obtained in c, wherein subsequent to the detecting, renal injuries are treated or wherein when said elevated levels of Chac1 and/or Angptl7 expression are detected, kidney-protective therapy is instituted.

* * * * *